US008428726B2

(12) United States Patent
Ignagni et al.

(10) Patent No.: US 8,428,726 B2
(45) Date of Patent: Apr. 23, 2013

(54) DEVICE AND METHOD OF NEUROMODULATION TO EFFECT A FUNCTIONALLY RESTORATIVE ADAPTION OF THE NEUROMUSCULAR SYSTEM

(75) Inventors: Anthony R. Ignagni, Oberlin, OH (US); Raymond P. Onders, Shaker Heights, OH (US)

(73) Assignee: Synapse Biomedical, Inc., Oberlin, OH (US)

( * ) Notice: Subject to any disclaimer, the term of this patent is extended or adjusted under 35 U.S.C. 154(b) by 257 days.

(21) Appl. No.: 12/690,410

(22) Filed: Jan. 20, 2010

(65) Prior Publication Data

US 2010/0198296 A1     Aug. 5, 2010

Related U.S. Application Data

(63) Continuation-in-part of application No. 12/261,979, filed on Oct. 30, 2008.

(60) Provisional application No. 61/145,935, filed on Jan. 20, 2009, provisional application No. 60/983,915, filed on Oct. 30, 2007.

(51) Int. Cl.
    *A61N 1/18*      (2006.01)
(52) U.S. Cl.
    USPC .......................................................... 607/42
(58) Field of Classification Search .................. 607/42
    See application file for complete search history.

(56) References Cited

U.S. PATENT DOCUMENTS

| | | | |
|---|---|---|---|
| 1,693,734 A | 12/1928 | Waggoner |
| 2,532,788 A | 12/1950 | Sarnoff |
| 2,664,880 A | 1/1954 | Wales, Jr. |
| 4,699,875 A | 10/1987 | Appel |
| 4,827,935 A | 5/1989 | Geddes et al. |
| 4,830,008 A | 5/1989 | Meer |
| 4,989,617 A | 2/1991 | Memberg et al. |
| 5,056,519 A | 10/1991 | Vince |
| 5,146,918 A | 9/1992 | Kallok et al. |
| 5,314,463 A | 5/1994 | Camps et al. |
| 5,368,035 A | 11/1994 | Hamm et al. |

(Continued)

FOREIGN PATENT DOCUMENTS

| EP | 996482 A1 | 5/2000 |
|---|---|---|
| EP | 873155 B1 | 6/2003 |

(Continued)

OTHER PUBLICATIONS

Zifko et al.; Central and peripheral respiratory electrophysiological studies in myotonic dystrophy; Brain; vol. 119; 1996; pp. 1911-1922.

(Continued)

*Primary Examiner* — Carl H Layno
*Assistant Examiner* — Jessica Sarcione
(74) *Attorney, Agent, or Firm* — Shay Glenn LLP

(57) ABSTRACT

Described herein are methods and systems for improving or adapting a breathing pattern of a patient with disordered breathing toward a more helpful state, as well as systems and devices for adapting breathing. These methods and systems may be used for improving sleep in patients with sleep disordered breathing and a system by which to implement devices for performing these methods.

18 Claims, 11 Drawing Sheets

U.S. PATENT DOCUMENTS

| | | | |
|---|---|---|---|
| 5,429,636 A | 7/1995 | Shikhman et al. | |
| 5,472,438 A | 12/1995 | Schmit et al. | |
| 5,483,969 A | 1/1996 | Testerman et al. | |
| 5,524,632 A | 6/1996 | Stein et al. | |
| 5,527,358 A | 6/1996 | Mehmanesh et al. | |
| 5,678,535 A | 10/1997 | DiMarco | |
| 5,716,392 A | 2/1998 | Bourgeois et al. | |
| 5,718,248 A | 2/1998 | Trumble et al. | |
| 5,792,165 A | 8/1998 | Klieman et al. | |
| 5,797,923 A | 8/1998 | Aiyar et al. | |
| 5,813,399 A | 9/1998 | Isaza et al. | |
| 5,814,086 A | 9/1998 | Hirschberg et al. | |
| 5,849,290 A | 12/1998 | Brown et al. | |
| 5,851,783 A | 12/1998 | Appel et al. | |
| 6,035,856 A | 3/2000 | LaFontaine et al. | |
| 6,194,217 B1 | 2/2001 | Matson | |
| 6,198,970 B1 | 3/2001 | Freed et al. | |
| 6,210,970 B1 | 4/2001 | Matson | |
| 6,245,053 B1 | 6/2001 | Benjamin | |
| 6,254,425 B1 | 7/2001 | Shchervinsky et al. | |
| 6,311,692 B1 | 11/2001 | Vaska et al. | |
| 6,321,109 B2 | 11/2001 | Ben-Haim et al. | |
| 6,360,740 B1 | 3/2002 | Ward et al. | |
| 6,397,108 B1 | 5/2002 | Camps et al. | |
| 6,405,732 B1 | 6/2002 | Edwards et al. | |
| 6,415,183 B1 | 7/2002 | Scheiner et al. | |
| 6,463,327 B1 | 10/2002 | Lurie et al. | |
| 6,477,423 B1 | 11/2002 | Jenkins | |
| 6,571,127 B1 | 5/2003 | Ben-Haim et al. | |
| 6,645,145 B1 | 11/2003 | Dreschel et al. | |
| 6,845,271 B2 | 1/2005 | Fang et al. | |
| 6,918,871 B2 | 7/2005 | Schulze | |
| 6,947,792 B2 | 9/2005 | Ben-Haim et al. | |
| 7,006,871 B1 | 2/2006 | Darvish et al. | |
| 7,044,921 B2 | 5/2006 | Asmus et al. | |
| 7,071,194 B2 | 7/2006 | Teng | |
| 7,107,092 B2 | 9/2006 | Goldstein et al. | |
| 7,120,497 B2 | 10/2006 | Ben-Haim et al. | |
| 7,155,278 B2 | 12/2006 | King et al. | |
| 7,165,551 B2 | 1/2007 | Edwards et al. | |
| 7,195,881 B2 | 3/2007 | Geffard | |
| 7,206,636 B1 | 4/2007 | Turcott | |
| 7,207,946 B2 | 4/2007 | Sirokman | |
| 7,221,978 B2 | 5/2007 | Ben-Haim et al. | |
| 7,225,016 B1 | 5/2007 | Koh | |
| 7,329,489 B2 | 2/2008 | Kaddurah-Daouk et al. | |
| 7,356,521 B2 | 4/2008 | Wang et al. | |
| 7,418,298 B2 | 8/2008 | Shiroff et al. | |
| 2001/0025177 A1 | 9/2001 | Woloszko et al. | |
| 2001/0049497 A1 | 12/2001 | Kalloo et al. | |
| 2002/0103424 A1 | 8/2002 | Swoyer et al. | |
| 2003/0040785 A1 | 2/2003 | Maschino et al. | |
| 2003/0148404 A1 | 8/2003 | Michaelson | |
| 2003/0171672 A1 | 9/2003 | Varghese et al. | |
| 2003/0175832 A1 | 9/2003 | Marton et al. | |
| 2003/0195600 A1 | 10/2003 | Tronnes et al. | |
| 2004/0003813 A1 | 1/2004 | Banner et al. | |
| 2004/0044377 A1 | 3/2004 | Larsson | |
| 2004/0064069 A1 | 4/2004 | Reynolds et al. | |
| 2004/0122360 A1 | 6/2004 | Waldhauser et al. | |
| 2004/0167437 A1 | 8/2004 | Sharrow et al. | |
| 2004/0167442 A1 | 8/2004 | Shireman et al. | |
| 2004/0167443 A1 | 8/2004 | Shireman et al. | |
| 2004/0172090 A1 | 9/2004 | Janzig et al. | |
| 2004/0177388 A1 | 9/2004 | Botas et al. | |
| 2004/0254572 A1 | 12/2004 | McIntyre et al. | |
| 2004/0260198 A1 | 12/2004 | Rothberg et al. | |
| 2004/0260245 A1 | 12/2004 | Clem et al. | |
| 2004/0260246 A1 | 12/2004 | Desmond | |
| 2004/0260337 A1 | 12/2004 | Freed | |
| 2005/0021102 A1 | 1/2005 | Ignagni et al. | |
| 2005/0033394 A1 | 2/2005 | Seifert et al. | |
| 2005/0042589 A1* | 2/2005 | Hatlestad et al. | 434/262 |
| 2005/0049523 A1 | 3/2005 | Crank | |
| 2005/0054950 A1 | 3/2005 | Parins | |
| 2005/0054951 A1 | 3/2005 | Parins | |
| 2005/0054952 A1 | 3/2005 | Eskuri et al. | |
| 2005/0080463 A1 | 4/2005 | Stahmann et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0107781 A1 | 5/2005 | Ostrovsky et al. | |
| 2005/0107812 A1 | 5/2005 | Starksen et al. | |
| 2005/0107860 A1 | 5/2005 | Ignagni et al. | |
| 2005/0109340 A1 | 5/2005 | Tehrani | |
| 2005/0113710 A1 | 5/2005 | Stahmann et al. | |
| 2005/0115561 A1 | 6/2005 | Stahmann et al. | |
| 2005/0124917 A1 | 6/2005 | Skujins et al. | |
| 2005/0137501 A1 | 6/2005 | Euteneuer et al. | |
| 2005/0148026 A1 | 7/2005 | Bowser et al. | |
| 2005/0148818 A1 | 7/2005 | Mesallum | |
| 2005/0165457 A1 | 7/2005 | Benser et al. | |
| 2005/0209653 A1 | 9/2005 | Herbert et al. | |
| 2005/0240241 A1 | 10/2005 | Yun et al. | |
| 2005/0277945 A1 | 12/2005 | Saadat et al. | |
| 2006/0030894 A1 | 2/2006 | Tehrani | |
| 2006/0035849 A1 | 2/2006 | Spiegelman et al. | |
| 2006/0036294 A1 | 2/2006 | Tehrani | |
| 2006/0041022 A1 | 2/2006 | Pasinetti | |
| 2006/0068452 A1 | 3/2006 | Goldknopf et al. | |
| 2006/0088862 A1 | 4/2006 | Lee | |
| 2006/0115854 A1 | 6/2006 | Goldknopf et al. | |
| 2006/0115855 A1 | 6/2006 | Goldknopf et al. | |
| 2006/0115856 A1 | 6/2006 | Goldknopf et al. | |
| 2006/0115867 A1 | 6/2006 | Goldknopf et al. | |
| 2006/0121619 A1 | 6/2006 | Bowser | |
| 2006/0122662 A1 | 6/2006 | Tehrani et al. | |
| 2006/0130161 A1 | 6/2006 | Genain | |
| 2006/0130833 A1 | 6/2006 | Younes | |
| 2006/0142815 A1 | 6/2006 | Tehrani et al. | |
| 2006/0149316 A1 | 7/2006 | DeVries et al. | |
| 2006/0149334 A1 | 7/2006 | Tehrani et al. | |
| 2006/0155222 A1 | 7/2006 | Sherman et al. | |
| 2006/0155341 A1 | 7/2006 | Tehrani et al. | |
| 2006/0160087 A1 | 7/2006 | McGrath et al. | |
| 2006/0167523 A1 | 7/2006 | Tehrani et al. | |
| 2006/0200004 A1 | 9/2006 | Wilk | |
| 2006/0224209 A1 | 10/2006 | Meyer | |
| 2006/0247729 A1 | 11/2006 | Tehrani et al. | |
| 2006/0258667 A1 | 11/2006 | Teng | |
| 2006/0281809 A1 | 12/2006 | Miller et al. | |
| 2006/0282131 A1 | 12/2006 | Caparso et al. | |
| 2006/0286167 A1 | 12/2006 | Staunton et al. | |
| 2006/0287679 A1 | 12/2006 | Stone | |
| 2007/0017809 A1 | 1/2007 | Goldknopf et al. | |
| 2007/0021421 A1 | 1/2007 | Hampton | |
| 2007/0021500 A1 | 1/2007 | Twyman et al. | |
| 2007/0021795 A1 | 1/2007 | Tehrani | |
| 2007/0038127 A1 | 2/2007 | Goldstein et al. | |
| 2007/0049793 A1 | 3/2007 | Ignagni et al. | |
| 2007/0054852 A1 | 3/2007 | Lin et al. | |
| 2007/0072943 A1 | 3/2007 | Miller et al. | |
| 2007/0078099 A1 | 4/2007 | McLaurin | |
| 2007/0087000 A1 | 4/2007 | Walsh et al. | |
| 2007/0087314 A1 | 4/2007 | Gomo | |
| 2007/0098812 A1 | 5/2007 | Feinstein et al. | |
| 2007/0117772 A1 | 5/2007 | Bennett et al. | |
| 2007/0118183 A1 | 5/2007 | Gelfand et al. | |
| 2007/0122813 A1 | 5/2007 | Salomon et al. | |
| 2007/0150006 A1 | 6/2007 | Libbus et al. | |
| 2007/0150023 A1 | 6/2007 | Ignagni et al. | |
| 2007/0172820 A1 | 7/2007 | Kaddurah-Daouk et al. | |
| 2007/0191908 A1 | 8/2007 | Jacob et al. | |
| 2007/0196780 A1 | 8/2007 | Ware et al. | |
| 2007/0197932 A1 | 8/2007 | Feke et al. | |
| 2007/0202515 A1 | 8/2007 | Hadlock et al. | |
| 2007/0202537 A1 | 8/2007 | Lingappa et al. | |
| 2007/0221224 A1 | 9/2007 | Pittman et al. | |
| 2007/0225261 A1 | 9/2007 | Miller et al. | |
| 2007/0240718 A1 | 10/2007 | Daly | |
| 2007/0250162 A1 | 10/2007 | Royalty | |
| 2007/0265611 A1 | 11/2007 | Ignagni et al. | |
| 2007/0274992 A1 | 11/2007 | Michalovich et al. | |
| 2007/0282388 A1 | 12/2007 | Sandyk | |

| | | | |
|---|---|---|---|
| 2007/0292403 | A1 | 12/2007 | Nivaggioli |
| 2007/0292410 | A1 | 12/2007 | Cashman et al. |
| 2007/0298998 | A1 | 12/2007 | Paige et al. |
| 2008/0003208 | A1 | 1/2008 | Nivaggioli |
| 2008/0097153 | A1 | 4/2008 | Ignagni et al. |
| 2008/0121231 | A1 | 5/2008 | Sinderby et al. |
| 2008/0125828 | A1 | 5/2008 | Ignagni et al. |
| 2008/0188867 | A1 | 8/2008 | Ignagni et al. |
| 2008/0287820 | A1 | 11/2008 | Onders et al. |
| 2009/0118785 | A1 | 5/2009 | Ignagni et al. |
| 2010/0125310 | A1* | 5/2010 | Wilson et al. ............ 607/42 |
| 2011/0060381 | A1 | 3/2011 | Ignagni et al. |

FOREIGN PATENT DOCUMENTS

| | | |
|---|---|---|
| EP | 1634617 A1 | 3/2006 |
| EP | 1653863 A2 | 5/2006 |
| EP | 1658020 A1 | 5/2006 |
| EP | 1660177 A1 | 5/2006 |
| EP | 1663370 A2 | 6/2006 |
| EP | 1667757 A2 | 6/2006 |
| EP | 1670611 A2 | 6/2006 |
| EP | 1684655 A2 | 8/2006 |
| EP | 1393773 B1 | 10/2006 |
| EP | 1306104 B1 | 1/2007 |
| EP | 1205202 B1 | 6/2007 |
| WO | WO 86/00234 A1 | 1/1986 |
| WO | WO 2005/039691 A1 | 5/2005 |
| WO | WO 2005/044079 A2 | 5/2005 |
| WO | WO 2006/062710 A1 | 6/2006 |
| WO | WO 2006/079152 A1 | 8/2006 |
| WO | WO 2006/083675 A2 | 8/2006 |
| WO | WO 2006/088696 A2 | 8/2006 |
| WO | WO 2006/121447 A2 | 11/2006 |
| WO | WO 2006/124023 A1 | 11/2006 |
| WO | WO 2006/131150 A1 | 12/2006 |
| WO | WO 2006/138069 A1 | 12/2006 |
| WO | WO 2007/035804 A2 | 3/2007 |
| WO | WO 2007/053230 A2 | 5/2007 |
| WO | WO 2007/058780 A2 | 5/2007 |
| WO | WO 2007/058938 A2 | 5/2007 |
| WO | WO 2007/061902 A2 | 5/2007 |
| WO | WO 2007/082384 A1 | 7/2007 |
| WO | WO 2007/103585 A2 | 9/2007 |
| WO | WO 2007/109443 A2 | 9/2007 |
| WO | WO 2007/128002 A2 | 11/2007 |

OTHER PUBLICATIONS

Ayas et al; Prevention of human diaphragm atrophy with short periods of electrical stimulation; Am J Respir Crit Care Med; vol. 159; pp. 2018-2020; 1999.

Bhadra et al.; Extraction force and tissue change during removal of a tined intramuscular electrode from rat gastrocnemius; Annals of Biomedical Engineering; vol. 34; No. 6; pp. 1042-1050; Jun. 2006.

DeCarvalho et al.; Motor neuron disease presenting with respiratory failure; Journal of the Neurological Sciences; vol. 139; No. Suppl.; 1996; pp. 117-122.

DiMarco et al.; Phrenic nerve pacing in a tetraplegic patient via intramuscular diaphragm electrodes; American Journal of Respiratory and Critical Care Medicine; vol. 166 (12 Pt 1); pp. 1604-1606; Dec. 15, 2002.

DiMarco A. F.; Restoration of respiratory muscle function following spinal cord injury—Review of electrical and magnetic stimulation techniques; Respiratory Physiology & Neurobiology; 147; 273-287; 2005.

Kalloo et al.; Flexible transgastric peritoneoscopy: a novel approach to diagnosis and therapeutic intervention in the peritoneal cavity; Gastrointestinal Endoscopy; vol. 60; No. 1; pp. 114-117; 2004.

Knutson et al.; Electrode fracture rates and occurrences of infection and granuloma associated with percutaneous intramuscular electrodes in upper-limb functional electrical stimulation applications; Journal of Rehabilitation Research and Development; vol. 39; No. 6; pp. 671-684, Nov./Dec. 2002.

Nochomovitz et al.; Conditioning of the diaphragm with phrenic nerve stimulation after prolonged disuse; American Review of Respiratory Disease; vol. 130; No. 4; 325-329; Oct. 1984.

Nochomovitz et al.; Diaphragm activation with intramuscular stimulation in dogs; American Review of Respiratory Disease; vol. 127; No. 3; 685-687; Mar. 1983.

Onders et al.; Early results of laparoscopic motor point diaphragm pacing in amyotrophic lateral sclerosis; Amyotrophic Lateral Sclerosis (Abstracts from the 16th Intl. Symp. ALS/MND; vol. 6, supp. 1; ISSN1743-4475; pp. 142-143; Dec. 2005.

Onders et al.; Mapping the phrenic nerve motor point: the key to a successful laparoscopic diaphragm pacing system in the first human series; Surgery; vol. 136; No. 4; 819-26; Oct. 2004.

Peterson et al.; Long-term intramuscular electrical activation of the phrenic nerve: Safety and reliability; IEEE; vol. 41; No. 12; pp. 1115-1126; Dec. 1994.

Peterson et al.; Electrical activation of respiratory muscles by methods other than phrenic nerve cuff electrodes; Pacing and Clinical Electrophysiology; vol. 12; No. 5; pp. 854-878; May 1989.

Peterson et al.; Intramuscular electrical activation of the phrenic nerve; IEEE Transactions on Biomedical Engineering; vol. BME-33; No. 3; 342-351; Mar. 1986.

Polkey et al.; Influence of acute lung volume change on contractile properties of human diaphragm; Journal of Applied Physiology; vol. 85, No. 4; pp. 1322-1328; Oct. 1998.

Sarnoff et al.; Electrophrenic respiration; Science; vol. 108; 482; Oct. 29, 1948.

Schmit, et al.; Laparoscopic placement of electrodes for diaphragm pacing using stimulation to locate the phrenic nerve motor points; IEEE Trans on Rehab Engineer; vol. 6; No. 4; 382-390; Dec. 1998.

Stewart et al.; Electromyography of respiratory muscles in amyotrophic lateral sclerosis; Journal of the Neurological Sciences; vol. 191; No. 1-2; Oct. 15, 2001; pp. 67-73.

de Carvalho et al.; Medical technology assessment: Electrodiagnosis in motor neuron diseases and amyotrophic lateral sclerosis; Neurophysiol. Clin.; Oct. 2001; 31 (5); pp. 341-348.

* cited by examiner

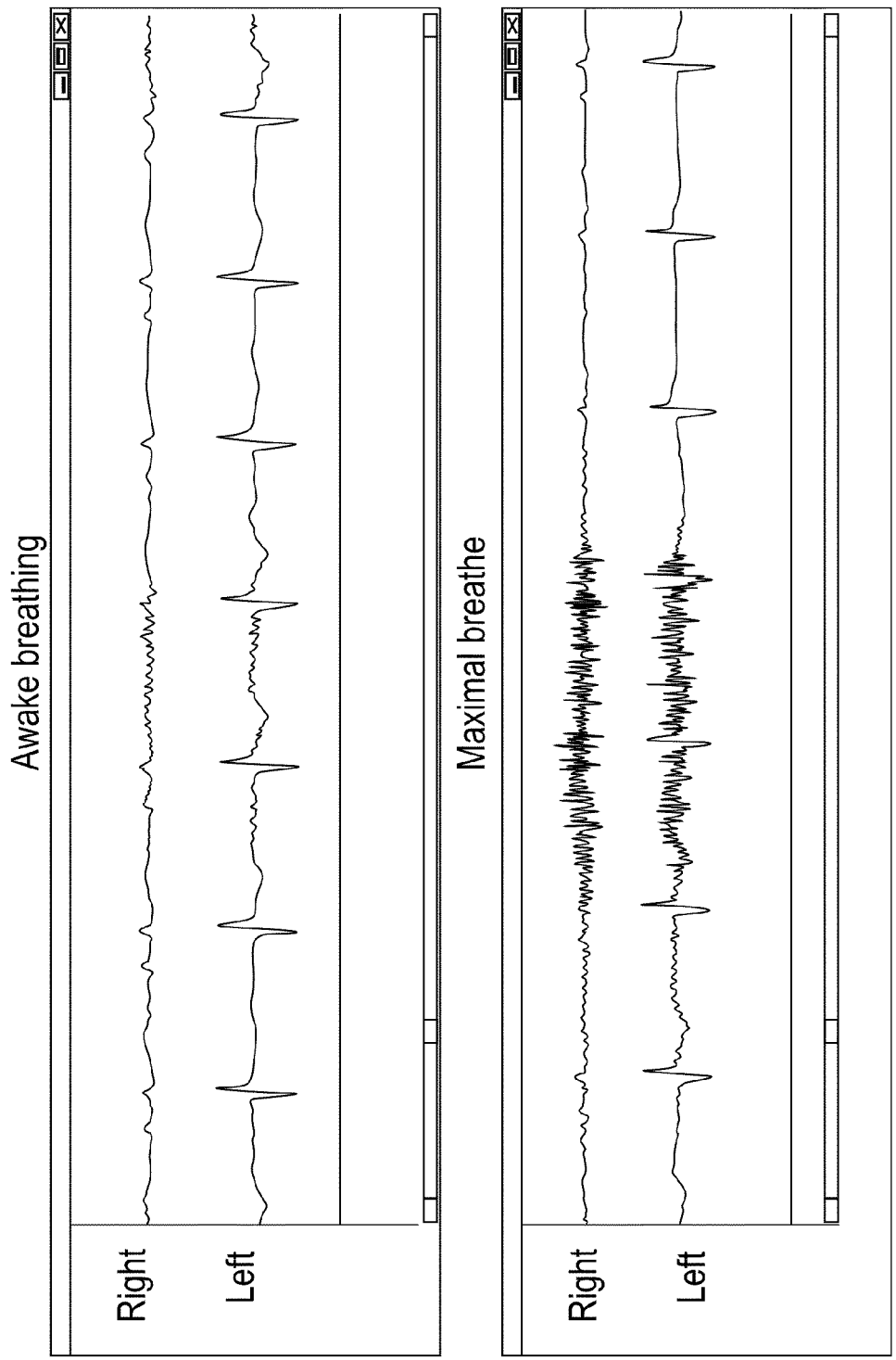

Oxygen Desaturation in split sleep study of ALS patient on BiPAP

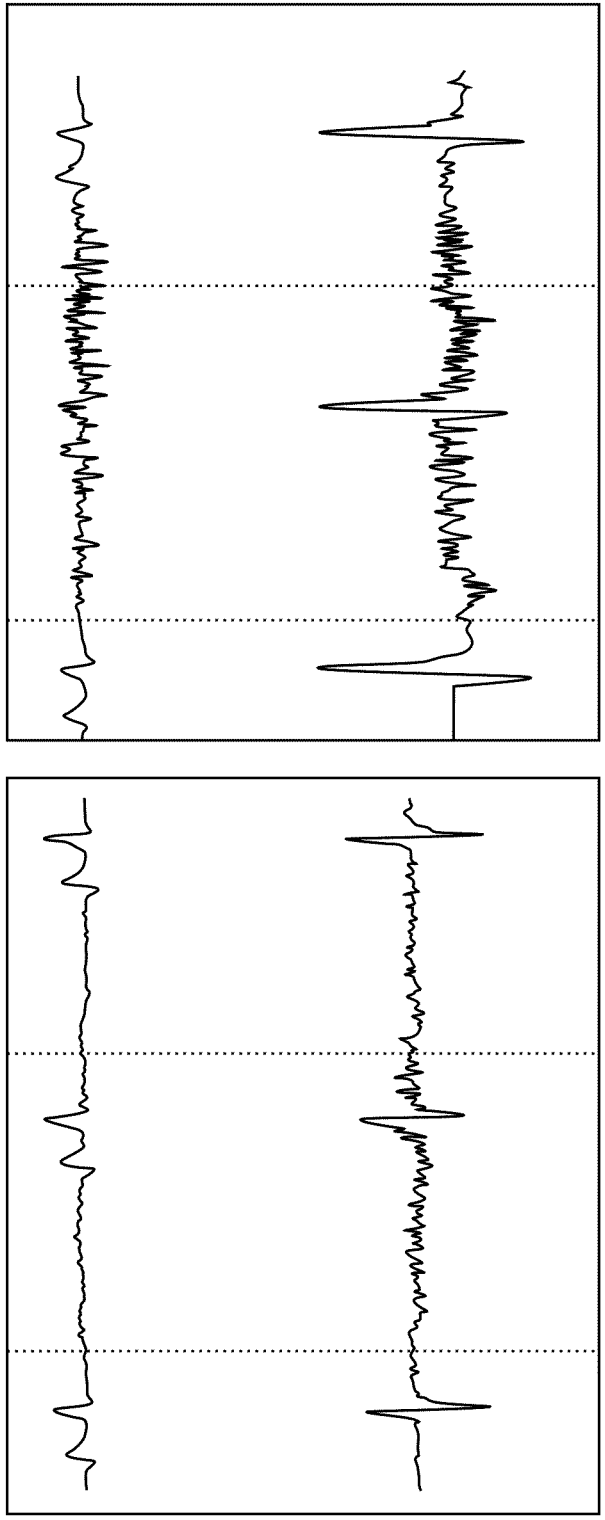

DEVICE AND METHOD OF NEUROMODULATION TO EFFECT A FUNCTIONALLY RESTORATIVE ADAPTION OF THE NEUROMUSCULAR SYSTEM

CROSS REFERENCE TO RELATED APPLICATIONS

This patent application claims priority to U.S. Provisional Patent Application No. 61/145,935, titled "DEVICE AND METHOD OF NEUROMODULATION TO EFFECT A FUNCTIONALLY RESTORATIVE ADAPTATION OF NEUROMUSCULAR SYSTEM" filed on Jan. 20, 2009 (now expired).

This patent application also claims priority as a Continuation-in-Part of U.S. patent application Ser. No. 12/261,979, titled "METHOD OF IMPROVING SLEEP DISORDERED BREATHING" filed Oct. 30, 2008 (published on May 7, 2009, as U.S. Publication No. 2009/0118785 A1), which claims priority to U.S. Provisional. Patent Application No. 60/983,915 "METHOD OF IMPROVING SLEEP DISORDERED BREATHING" filed on Oct. 30, 2007 (now expired).

INCORPORATION BY REFERENCE

All publications and patent applications mentioned in this specification are herein incorporated by reference in their entirety and to the same extent as if each individual publication or patent application were specifically, individually, and explicitly incorporated by reference in their entirety.

FIELD OF THE INVENTION

The invention relates to apparatus and methods for improving the quality of sleep in patients who have or are at risk of having sleep-disordered breathing. In particular, the apparatus and methods described herein relate to treatment of patients with disorders impacting upper motor neurons, including those with amyotrophic lateral sclerosis (ALS) and central sleep apnea. The invention also relates to systems and methods for treating malfunctioning neuromuscular pathways through the application of neurostimulation to cause a reflexive or automatic functional outcome. One embodiment is a treatment for sleep disordered breathing, and more particularly a therapeutic restoration or adaptive regaining of breathing ability through neuromodulation or neurostimulation to a more healthful state wherein the need for other forms of breath-supportive therapy is diminished or eliminated.

BACKGROUND OF THE INVENTION

Patients with neuromuscular diseases such as amyotrophic lateral sclerosis often suffer from central nervous system-mediated sleep disorders that can cause orthopnea, nocturnal hypoventilation, and a reduction in REM sleep. Noninvasive positive pressure ventilation (NIPPV) therapy in the form of with bi-level positive airway pressure (BiPAP) or continuous positive airway pressure CPAP) is commonly provided to these patients, with some success, in an effort to restore sleep toward normal. Further, NIPPV therapy has been shown to increase survival times of ALS patients. However, a significant percentage of patients do not tolerate the positive pressure intervention well, at least in part because of bulbar symptoms, such as difficulty with management of swallowing, saliva, aspiration, and communication, or other coping issues. Other therapeutic approaches to improving the quality of sleep in patients with neuromuscular diseases and associated central nervous system mediated disorders of sleep are desirable.

The therapeutic use of neuromodulation or neurostimulation in order to create a change in nerve conduction or muscle function at the site such modulation or stimulation has met with some success in various therapeutic circumstances. For example, periodic stimulation by spinal cord stimulators has been used to block pain sensation, periodic stimulation by deep brain stimulation (DBS) methodology has been used to block tremors, functional electrical stimulation (FES) has been able to create movement, periodic stimulation by vagus nerve stimulation (VNS) methodology has been able to block epileptic seizures, and intermittent stimulation by VNS has been shown to block hunger signals and create a sensation of satiety.

It would be desirable to have neuromodulatory or neurostimulatory therapeutic modalities available that would encourage a functionally beneficial outcome by introducing reflexive or automatic pathways that would work in conjunction with the applied therapy. This could be applied, for example, to conditions that compromise breathing particularly as it occurs during sleep, as in sleep apnea.

SUMMARY OF THE INVENTION

The invention provided herein includes methods of improving or adapting a breathing pattern of a patient with disordered breathing toward a more helpful state, as well as systems and devices for adapting breathing. In some variations, described herein are methods and systems for improving sleep in patients with sleep disordered breathing and a system by which to implement devices for performing these methods.

For example, a method for adapting a breathing pattern of a patient with disordered breathing toward a more healthful state may include: implanting a neurostimulatory device in the diaphragm of the patient; stimulating the diaphragm; evaluating the patient's diaphragm by electromyographic (EMG) methodology to determine the effectiveness of the establishment of an automatic, reflexive, or synchronized breathing mechanism. The method may also include the step of evaluating the patient by polysomnographic (PSG) methodology to assess diminishment of sleep disordered breathing.

Also described herein are methods to entrain breathing comprising repetitively applying low-levels of physiologically normal stimulation to establish a baseline automatic function.

For example, described herein are methods of restoring a compromised neurophysiological function comprising: applying electrical stimulation to a compromised target; displacing a maladapted physiological functioning; and establishing an appropriately coordinated function in a target and reflex pathway.

Also described herein are systems for adapting breathing of a patient with sleep-disordered breathing toward a more healthful state. The system may include: a neurostimulation device, the device including a stimulator and electrodes configured to be implanted and interface with a stimulated end target; an electromyographic activity monitor configured to display and/or process data from the electrodes; and a programming device to implement changes in levels and periodicity of applied signals based on electromyographic activity and functional need.

In some variations, the methods and devices described herein may be used during or for sleep. For example, described herein are systems for improving breathing (and/or sleep) in a patient with centrally-mediated sleep disordered breathing may include an electronic signal generator, one or more electrodes operably connected to the signal generator, the one or more electrodes configured to stimulate a diaphragm, an electromyographic (EMG) processor arranged to capture EMG activity data of the diaphragm while being paced by the one or more electrodes, and a sleep sequencer configured to integrate any combination of stimulation parameter input, respiratory parameter input, and EMG data, and to convey processed data from these inputs to the electronic signal generator. Embodiments of the electronic signal generator typically include a power supply, an impedance detector, a microcontroller, a waveform generator, and one or more signal drivers. In some embodiments, the EMG processor is configured to convey data to a display; in embodiments the EMG processor is configured to convey data to the sleep sequencer; in some embodiments, the EMG processor is configured to convey data both to a display and the sleep sequencer.

In some embodiments, the sleep sequencer is further configured to ramp up stimulus intensity to a threshold level. The sleep sequencer may be variously configured such that, for example, the stimulus intensity ramp up provides an increase in pulse duration followed by an increase in pulse amplitude, the stimulus intensity ramp up provides an increase in pulse amplitude followed by an increase in pulse duration, or the intensity ramp up may provide an interleaved increase in pulse amplitude and pulse duration. The sleep sequences may also be configured to provide a stimulus ramp up with various envelope forms; for example, the stimulus ramp may have a linear envelope, an exponential envelope, or it may have an arbitrarily-shaped envelope.

A method of improving sleep in a patient by using a system as summarized above, with one or more electrodes implanted in the diaphragm for stimulation of the diaphragm, may include adapting stimulation parameters to support respiration during sleep, and stimulating the diaphragm in a therapeutic regimen with the one or more electrodes to support respiration after the onset of sleep, the regimen including the adapted stimulation parameters. The stimulation typically operates independently of any voluntary respiratory effort of the patient or detection of such effort in terms of feedback from the diaphragm.

The method is therapeutically appropriate for various types of patients, thus prior to the adapting and stimulating steps, the method may include diagnosing a patient as having a neuromuscular disease, particularly those with a disorder impacting upper motor neurons, such as, for example, amyotrophic lateral sclerosis (ALS) and central sleep apnea. More generally, the method may include (prior to the adapting and stimulating steps) identifying the patient as being at risk for sleep disordered breathing. Such patents may be, for example, an ICU patient or a post-surgical patient. More particularly, a post-surgical patient at risk may be one who has undergone a bariatric procedure, as bariatric patients are already commonly at risk for sleep disordered breathing. Another general class of patients at risk for sleep disordered breathing includes any patient having an upper motor neuron dysfunction that results in temporary or permanent diaphragm paralysis.

The method as summarized above, prior to the adapting and stimulating steps, includes a procedure whereby one or more electrodes are implanted in the diaphragm of the patient. These electrodes are used during the adapting phase of the method, as summarized below, and in a therapeutic regimen that follows the adapting phase.

Continuing more specifically with the aspect of the method that involves patient selection, the method may include diagnosing the patient as having sleep-disordered breathing by any one or more criteria including morning headaches, daytime sleepiness, PSG recordings consistent with disordered sleep, diaphragm EMG recordings during sleep consistent with disordered sleep, or pulmonary function testing data consistent with disordered sleep. Further, in the event that sleep-disordered breathing is found, the method includes diagnosing the patient's sleep sleep-disordered breathing as being centrally-mediated.

With regard to the parameter-adapting aspect of the method, wherein particular values for stimulation parameters to support respiration during sleep are determined, the method may include determining any one or more of an appropriate time interval after the onset of sleep to lapse prior to initiating stimulation, a threshold level of stimulation sufficiently low so as to allow onset of sleep, a threshold level of stimulation sufficient to stimulate diaphragm contraction, or a threshold level sufficient to support breathing during sleep. By this aspect of the method, the therapeutic regimen can be tailored to the physiological status of the patient.

Embodiments of the method may further include monitoring the EMG of the patient during the therapeutic regimen. And in some embodiments of the method, stimulating the diaphragm to support respiration includes initiating a breath and supporting a breath to completion.

After implementing the therapeutic regimen, the method may further include evaluating the patient again for presence of sleep disordered breathing by any one or more same diagnostic criteria as above (i.e., morning headaches, daytime sleepiness, PSG recordings consistent with disordered sleep, diaphragm EMG recordings during sleep consistent with disordered sleep, or pulmonary function test data consistent with disordered sleep) in order to know whether the therapy has been effective or if a revision of the patient-specific parameters is indicated. Accordingly, in the event of a finding of continued presence of sleep-disordered breathing, the method may further include revising the adapted stimulation parameters, and implementing a revised therapeutic regimen for the patient based on the revised parameters, the regimen comprising stimulating the diaphragm with the one or more electrodes to support respiration.

With further regard to the stimulating step of the method, stimulating the diaphragm in a therapeutic regimen after the onset of sleep typically includes waiting for a period of time after the onset of sleep before initiating stimulation. Determining the appropriate wait time after onset of sleep to initiate diaphragm stimulation may include determining the onset of sleep by monitoring the level of one or more physiological parameters and determining when they fall below a threshold value, the parameters including any of the diaphragm EMG, an EEG, or body movement. Still further with regard to the stimulating step, stimulating the diaphragm in a therapeutic regimen includes gradually ramping the stimulation over time to a reach a steady state level of stimulation, as will be summarized in further detail below.

In another aspect of the invention, a method of improving sleep in a patient with sleep-disordered breathing or at risk thereof includes electrically stimulating the patient's diaphragm with a sleep-specific stimulation protocol: That stimulation protocol includes initiating a sleep onset process, ramping the stimulation to a first level that does not exceed a level at which sleep onset is interrupted, (the patient) initiating sleep, synchronizing a natural sleep respiratory rate with a rate supported by the stimulation while ramping stimulation to a second level which is sufficient to provide detectable diaphragm contraction, and ramping the stimulation to a third level which is sufficient to support breathing during sleep.

Ramping the electrical stimulation of the diaphragm, as it occurs in these various phases of the therapeutic method, to varying levels at various steps, may include increasing pulse duration and then increasing pulse amplitude, increasing pulse amplitude and then increasing pulse duration, or increasing pulse amplitude and pulse duration in an interleaved manner. With regard to the general form of the ramping, ramping may occur with a linear envelope, with an exponential envelope, or with an envelope of an arbitrary or irregular shape.

Prior to the electrically-stimulating step, the method may include determining any one or more of an appropriate time interval after the onset of sleep to lapse prior to initiating stimulation, a threshold level of stimulation sufficiently low so as to allow onset of sleep, a threshold level of stimulation sufficient to stimulate diaphragm contraction, or a threshold level sufficient to support breathing during sleep.

BRIEF DESCRIPTION OF THE FIGURES

FIGS. 3A and 3B provide EMG charts of the breathing of a conscious (awake) ALS patient who had been implanted with DPS electrodes 18 months prior to these EMG readings. FIG. 3A shows normal awake breathing; FIG. 3B shows maximal breathing.

FIG. 4A shows a Cheyne-Stokes type breathing pattern. FIG. 4B shows an EMG chart of the ALS patient breathing with and without diaphragm pacing ((DPS) support.

FIGS. 5A and 5B show EMG charts of an ALS patient showing an improvement in burst activity over the course of 11 weeks of DPS therapy. FIG. 5A shows an EMG chart recorded at the outset of the therapy. FIG. 5B shows an EMG chart recorded after 11 weeks of DPS therapy.

DETAILED DESCRIPTION OF THE INVENTION

Described herein are methods and devices for applying neurostimulation and/or neuromodulation to increase the ability of a breathing-compromised patient to breathe independently or more independently. The inventors have observed that, for example, when one hemi-diaphragm of a spinal cord (SC)-injured patient is stimulated, electromyographic activity may be elicited on the contralateral hemi-diaphragm. Further, when the diaphragm of a spinal cord-injured patient was stimulated, accessory muscles were also reflexively contracted. In ALS patients, treatment with diaphragm pacing stimulation may result in a gradual but ultimately marked adaptation of voluntary breathing. The initial application of diaphragm stimulation is typically unsynchronized with voluntary breathing and causes discomfort for the patient. Following several sessions of stimulation, however, the voluntary breathing may become time-synchronized with the diaphragm stimulation. This observation provided an early insight into the inventive concept of an automatic or reflexive function induced by the stimulation which is described herein.

The inventors have also observed that ALS patients can hold (inhibit) their breath (as can normal subjects) to a point where the volitional holding of breath is overridden, i.e., a dis-inhibition that stops breath-holding and allows breathing to continue. After a period of diaphragm pacing stimulation (DPS) training, however, one particular ALS patient (initially able to hold her breath) was unable to hold her breath at all (i.e., demonstrating a disinhibition of breath-holding ability). This observation suggested that a baseline automatic function had been established that moved into the physiological vacuum associated with the lost central communication from the respiratory centers.

Figure 6:
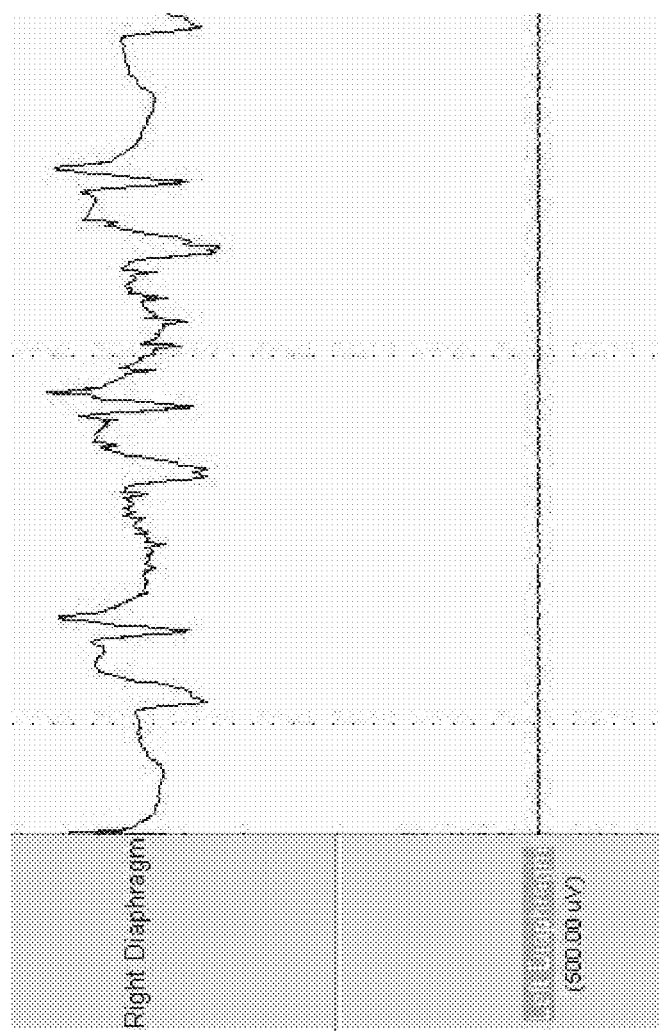
FIG. 6 shows a normal EMG of a right diaphragm of a patient that is synchronizing with the electrically-paced left diaphragm.
Figure 7:
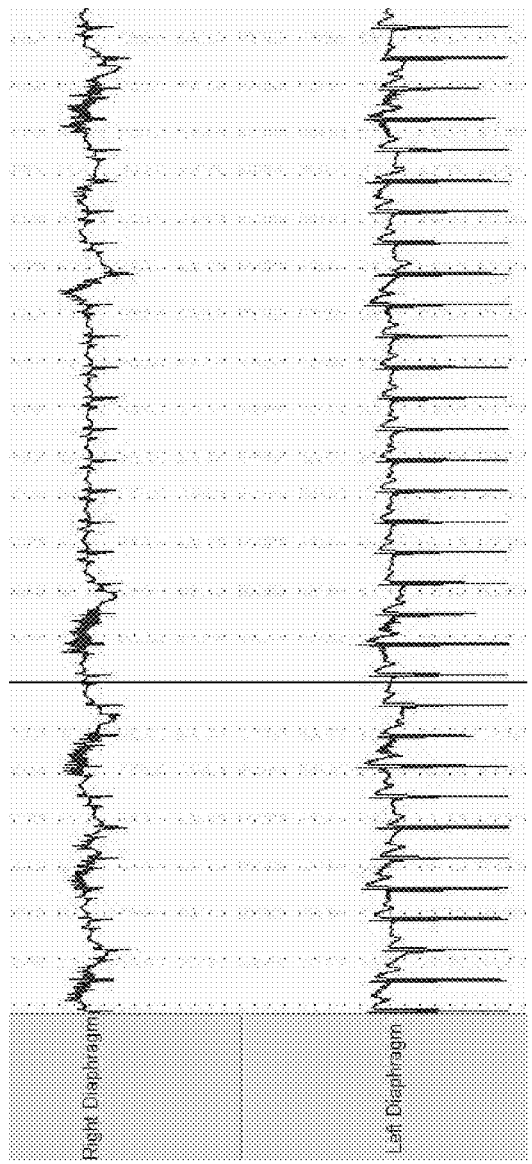
FIG. 7 shows the EMG of a patient prior to diaphragm pacing stimulation therapy able to hold her breath, with no visualized diaphragm EMG. This patient may have central sleep dysfunction and may be still early in the disease course.
Figure 8:
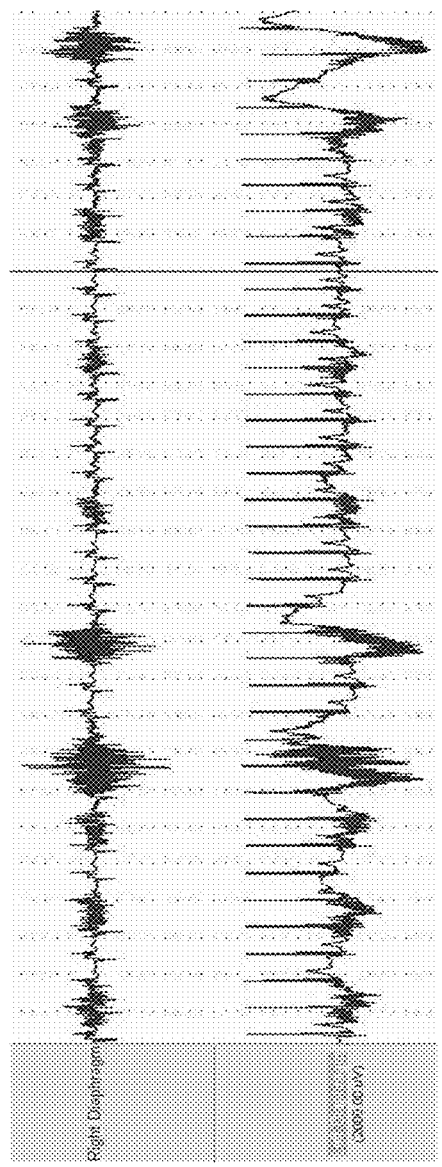
FIG. 8 shows the EMG of a patient (advanced in her ALS course) who has been treated with diaphragm pacing, and now has a rhythmic breathing pattern, but can no longer stop her breath, and thus shows breakthrough breathing.
Figure 9:
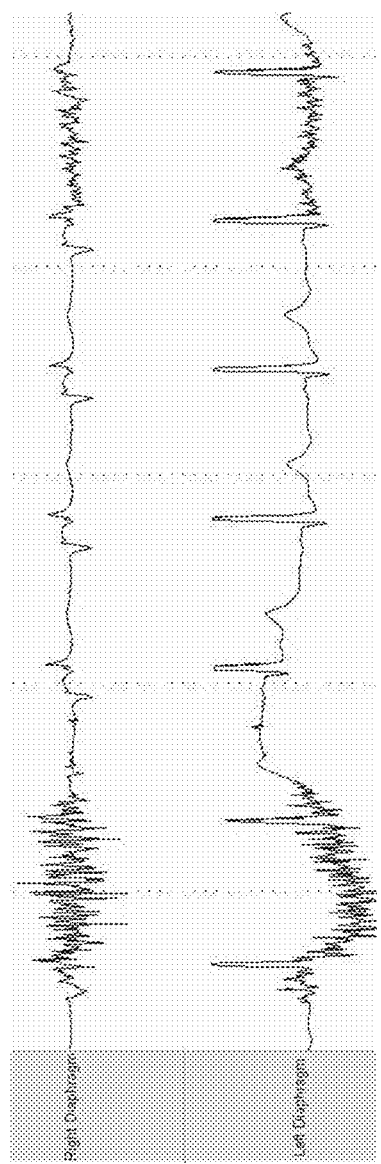
FIG. 9 provides a closer view of a five-second visualization of the same patient of FIG. 8, showing that the amount of diaphragm and perhaps the motor neurons that are involved in this breathing are different than during voluntary breathing.

The observations described above are illustrated in the EMG traces of FIGS. 6-9. FIG. 6 provides a 30-second view a normal EMG of a right diaphragm that is synchronizing with an electrically-paced left diaphragm. Pacing artifacts are evident in the EMG trace of the right diaphragm. These data are consistent with an afferent effect originating in the left diaphragm that is manifesting in contralateral accessory muscles. FIG. 7 provides a 30-second view of the EMG of a patient who has not yet received diaphragm pacing stimulation therapy who is able to hold her breath, with no visualized diaphragm EMG. This patient may have central sleep dysfunction and may be still early in the disease course. FIG. 8 provides a 30-second view of the EMG of a patient (advanced in her ALS course) who has been subjected to diaphragm pacing, and now has a rhythmic breathing pattern, but can no longer stop her breath, and thus shows breakthrough breathing. FIG. 9 provides a closer view of a five-second visualization of the same patient of FIG. 8, showing that the amount of diaphragm and perhaps the motor neurons that are involved in this breathing are different than during voluntary breathing.

Such data lead to and supports the inventive concept that natural physiological support (e.g., through the application of neurostimulation) to a functional physiological element (such as the diaphragm) can affect a larger physiological system (such as respiration) by eliciting centrally mediated automatic function (in conjunction with or autonomous from the applied therapy) and reflexive function that supports the applied therapy.

The invention described herein thus provides embodiments of a system and methods that make use of neuromodulation in the form of diaphragm stimulation to effect an adaptation of the neural and muscular components of breathing in breathing-compromised patients. This adaptation allows a greater degree of independent (autonomous, automatic, or naturally-supported and sustained) breathing. The development of such naturally-supported sustained breathing is a manifestation of neurologically adaptive process and the establishment of a more healthful state for the patient.

Embodiments of the system include a neurostimulatory device, which includes a stimulator and electrodes that interface (i.e., provide an artificial synapse) with the stimulated end target in the diaphragm; an electromyographic activity monitor that records and displays information through the implanted electrodes from the end target; and a programming device or controller to implement changes in levels and periodicity of applied signals based on electromyographic activity and functional need. In various embodiments, each of the enumerated components of the system may be controlled and operated independently of the other components. Embodiments of the neurostimulatory system may be applied toward treatment of both central sleep apnea and complex sleep apnea.

For example, when treating a patient with presumptive central sleep apnea, the therapeutic method may include the following steps:

First (1): Evaluating the patient by polysomnographic (PSG) methodology in order to diagnose the cause of sleep disordered breathing in a patient, and determining it to be central sleep apnea.

Second (2): Implanting a neurostimulatory device in the diaphragm of the patient.

Third (3): Stimulating the diaphragm with the device at a level either (3a) below the patient's movement or sensory threshold, or (3b or 3c) above the patient's movement or sensory threshold. Step (3a) involves: Stimulating the diaphragm at a level below movement/sensory threshold to create an automatic baseline pacing through reflex/afferent effects on the central respiratory drive centers. Step (3b) includes: Stimulating the diaphragm at a level above the movement or sensory threshold to support a diaphragm movement that is sufficient to ventilate the patient but remains comfortably tolerated. The initial sessions may occur while the patient is awake in order to provide adaptation of voluntary or intrinsic respiration with open loop stimulation. Once adaptation occurs, the patient typically sleeps with the device on throughout the night. The facilitation of the onset of sleep may occur by implementation of methods described in greater detail below. Step (3c) includes: Stimulating the diaphragm at a level above the movement or sensory threshold to create movement that is sufficient to ventilate patient but is also comfortably tolerated for the duration of 30 minute sessions. The diaphragm of the patient then conditions through electrode-stimulated exercise while the patient is awake to create an automatic breathing mechanism, this representing a disinhibition of the ability to hold a breath. This aspect of the method may require a "breakthrough breathing refresher" prior to sleep.

Fourth (4): Re-evaluating the patient by polysomnographic (PSG) methodology to assess diminishment or elimination of central sleep apnea.

Fifth (5): Evaluating the patient's diaphragm by electromyographic (EMG) methodology to determine the effectiveness of the establishment of an automatic breathing mechanism.

The steps of the above described method, particularly with regard to the simulating protocol, may vary depending on particulars of the central apnea, which may be due to ALS, non-hypercapnic, hypercapnic, or of congenital origin.

When treating a patient with a presumptive complex sleep apnea, the therapeutic method may include the following steps:

1. Evaluating the patient by polysomnographic (PSG) methodology in order to diagnose the cause of sleep disordered breathing in a patient, and determining it to be a complex sleep apnea, distinct from central sleep apnea.

2. Implanting a neurostimulatory device in the diaphragm of the patient.

3. Stimulating the diaphragm with the device at a level either below or above the patient's movement or sensory threshold.

4. Re-evaluating the patient's diaphragm by polysomnographic (PSG) methodology to assess diminishment or elimination of complex sleep apnea.

5. Evaluating the patient's diaphragm by electromyographic (EMG) methodology during obstructive episodes.

6. Applying continuous positive airway pressure (CPAP) therapy to eliminate obstructions as needed.

7. Increasing stimulation to increase upper airway pressure (as measured, for example, with maximal inspiratory pressure (MIP) during stimulation to level need to improve patency of airway opening.

8. Titrating CPAP, to diminish or eliminate necessity thereof, based on extent of obstructive apneic events.

9. Evaluating the patient's apneic status after stabilizing the final CPAP settings.

The neurophysiological adaption of the respiratory system, as described above in the context of improving the breathing of patients with sleep compromised breathing due to centrally-mediated apnea or complex apnea, has other therapeutic applications as well. One example is provided by the therapeutic adaptation of patients with daytime hypoventilation. Repetitive nighttime diaphragm pacing stimulation may be able to entrain automatic breathing that would otherwise slow during a daytime sleep period. Another example is provided by the plight of hospitalized ill patients who suffer temporarily compromised breathing. Patients who are ill due to a wide variety of conditions, but particularly those who have suffered respiratory arrest, are subject to temporarily compromised respiration and are often intubated at night due to insufficient respiration during sleep. Without such respiratory support patients, particularly elderly patients, can die. The neurostimulatory adaptive therapy described herein would be of considerable benefit to such patients.

The application of physiologically natural stimulation by way of electrodes may therefore induce the development of reflexive pathways in association with the stimulation, and thus have immediate (or less immediate) effects, which may be long-lasting. In the context of respiration, as described herein, accessory muscles working with the diaphragm through spinal reflex pathways or muscles controlling upper airway patency through central spinal sensory and/or reflex paths may be induced by the applied stimulation. It is also possible that some degree of neuroplastic recovery may contribute to functional recovery, but the development of physiologically appropriate reflexive pathways is considered the more likely basis by which the therapeutic method is effective.

The methods described herein can be broadly understood as a therapeutic intervention that provides neurological, or neuromuscular stimulation or modulation of a compromised and dysfunctional neuromuscular target, and by such stimulation, including variable periodicity, and varying period of rest between periods of stimulation, function is improved or restored. The inventive method and system are described in the particular context of disordered breathing and diaphragmatic function. The system and methods described herein may also be generally applied to other anatomical sites and their respective neuromuscular functionality, such as for example, the lower esophageal sphincter, which when compromised, can contribute to gastroesophageal reflux disease (GERD).

Also described herein are systems and methods of diaphragm pacing stimulation for the treatment of disordered sleep, including the treatment of disordered sleep (e.g., apnea) in patients with neuromuscular diseases such as amyotrophic lateral sclerosis (ALS). Embodiments of the invention may also be usefully applied to patients with neuromuscular diseases other than ALS who experience central nervous system-mediated sleep disordered breathing. Embodiments of the invention may also be applied as therapy for patients with sleep disordered breathing due to other forms of sleep pathology, including those not-mediated by the central nervous system, such as obstructive or mixed (complex) apnea. Further, embodiments of the invention may be applied to patients who are considered to be temporarily at risk of respiratory compromise or failure, as for example, would be associated with surgery, anesthesia, or during the period of post-operative recovery with diaphragm activity monitored by clinical personnel. Some embodiments of the invention may be applied to the support of sleep in patients in a chronic manner, such as patients with a neuromuscular disease, in which embodiments electrodes adapted for long-term or permanent residence may be used. Other embodiments of the invention may be applied to patients that are in temporary need of respiratory surveillance or support, such as surgical patients, in which embodiments electrodes adapted for temporary placement may be used.

Improving the sleep by implementation of the inventive method can be appreciated by the patient in subjective terms, as well as measurable in objective terms. For example, improving sleep may include increasing total sleep time per night and/or increasing total REM sleep time per night. In some of the embodiments whereby REM sleep time is increased, the method further includes alleviating severity of or preventing development of intensive care unit psychosis. In other embodiments, improving sleep includes decreasing the level of sleep disturbance, such disturbances including, for example, periods of restlessness or wakefulness. In still other embodiments, improving sleep includes supporting a regular breathing rate during sleep. In some embodiments in which a regular breathing rate is instilled in the patient, the regular breathing rate prevents the development of central hypoventilation syndrome (CHS), or alleviates the severity thereof. In addition to these various relatively immediate undesirable consequences of disturbed sleep, sleep disturbance can contribute to many other adverse outcomes, such as cardiovascular disease and hypertension, can accrue over the longer term.

Aspects of the system and method as applied to diaphragm conditioning and acute support for respiratory-compromised patients have been described in U.S. patent application Ser. No. 10/897,685, filed on Jul. 23, 2004, which was published as U.S. Pub. No. 2005/0021102 on Jan. 27, 2005 (now U.S. Pat. No. 7,840,270, which issued on Nov. 23, 2010), and in U.S. patent application Ser. No. 11/716,459, filed on Mar. 9, 2007 (now U.S. Pat. No. 7,962,215, which issued on Jun. 14, 2011).

Figure 1A:
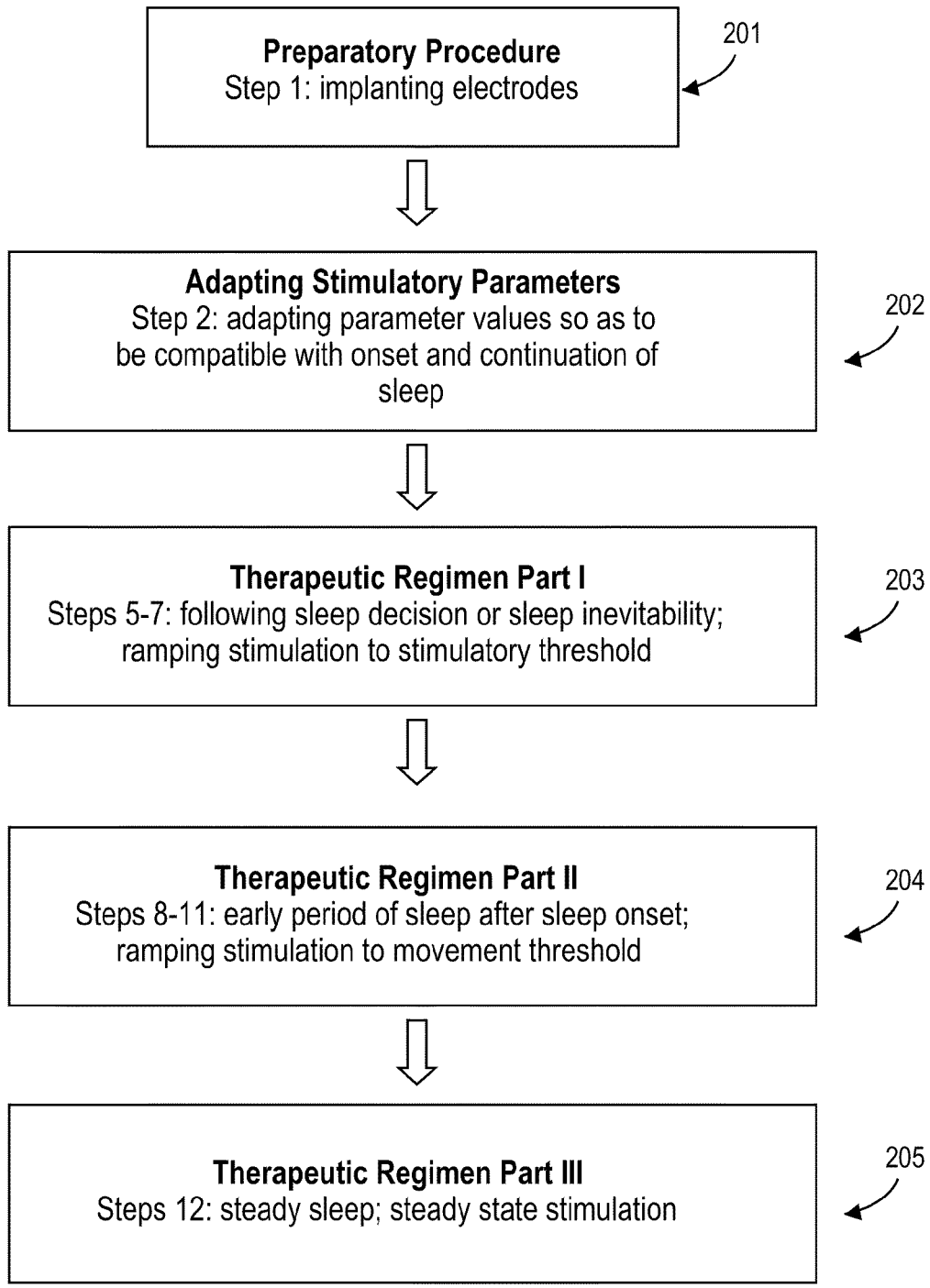
FIG. 1A provides a simplified block diagram of one variation of a method for treating disordered breathing as described herein.
Figure 1B:
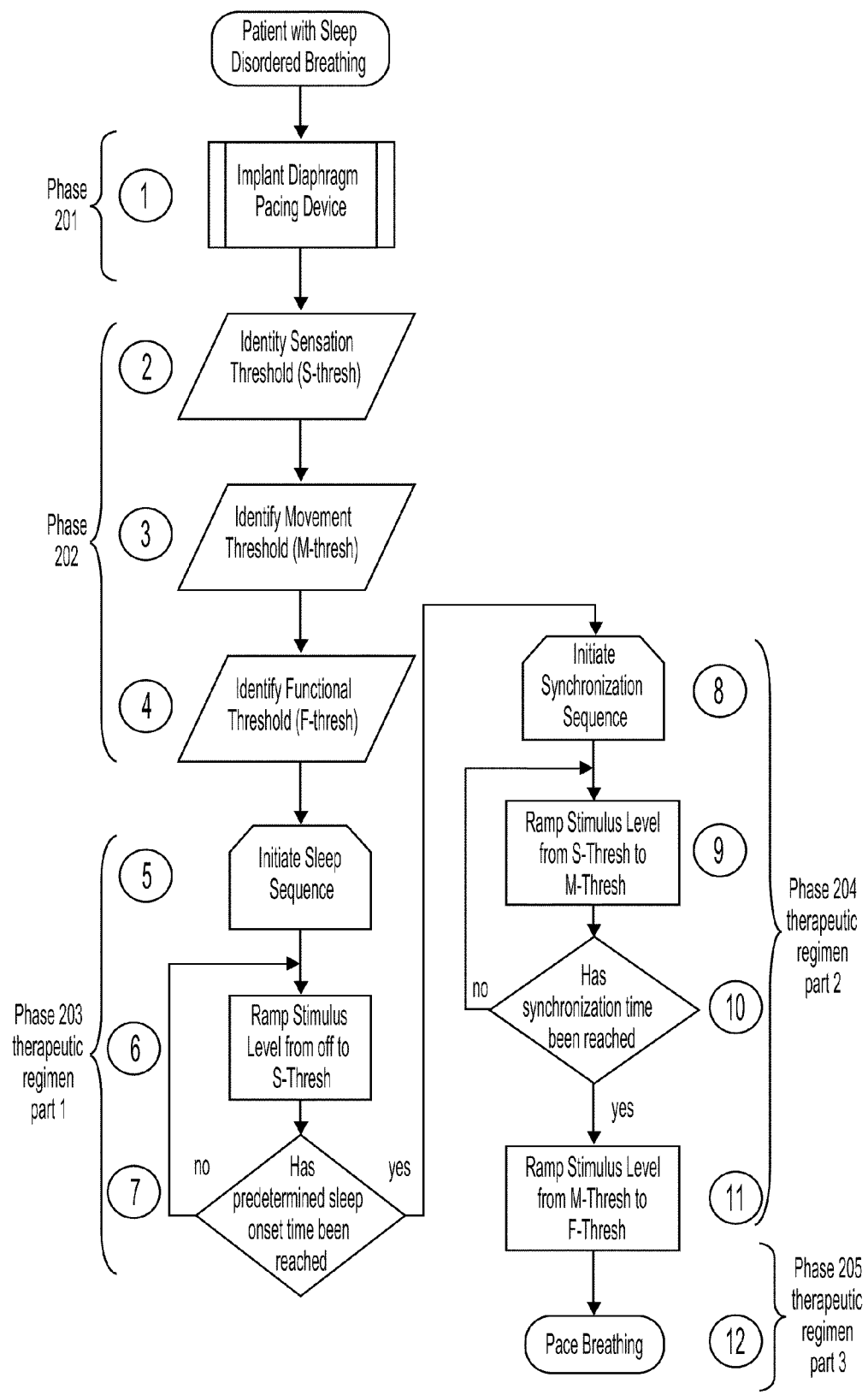
FIG. 1B provides an overview and further detail of a method of improving sleep-disordered breathing.

Returning now to FIGS. 1A-5b, an overview of the open loop method is provided in FIGS. 1A and 1B. FIG. 1A is a simplified flow diagram which outlines the method in terms of five phases (201-205), which are outlined in greater detail in FIG. 1B, including 12 steps. A preparatory aspect of the method 201 includes implanting diaphragm pacing electrodes in a patient. This is Step 1, as shown in FIG. 1B, and is detailed in further description below. In a preliminary aspect of the method 202, patient-specific stimulatory parameter values are determined in a series of Steps 5-7, as shown in FIG. 1B. A sleep-based therapeutic regimen that improves sleep-disordered breathing starts with an initial part 203 of a therapeutic regimen that occurs after a patient has made a decision to go to sleep, or after the patient has been observed to be in the early stages of falling asleep. This phase occurs in Steps 5-7, as shown in FIG. 1B. During this phase 203, stimulation is ramped up to a stimulatory threshold that was determined during the adapting phase 202 of the method. In a second part of the therapeutic regimen 204, which occurs after the onset of sleep, stimulation is ramped up to a movement threshold, as determined during the adapting phase 202 of the method. This phase 204 occurs over the course of Steps 8-11, as shown in FIG. 1B. In a third part of the therapeutic regimen 205, sleep is ongoing and steady and stimulation is being delivered at a steady state, as represented by Step 12 as shown in FIG. 1B.

FIG. 1B provides a more detailed view of the method, with individual steps included. Implantation of diaphragm pacing electrodes (Step 1) may be by way any of various conventional approaches, such as through laparoscopic approaches, a thoracic surgical approach, or by way of natural orifice transluminal endoscopic surgery (NOTES). Step 1 is a preparatory procedure, which may take place at a time identified by a physician, after consulting with the patient, at any reasonable time prior to initiating a therapeutic regimen. Steps 2-4 relate to aspects of the method that relate to adapting stimulation parameters to support respiration during sleep, such adapted parameters varying from patient-to-patient, and further, possibly varying with the patient over time. Steps 5-12 relate to aspects of the implemented regimen, adapted to the patient particulars as determined in Steps 2-4.

Steps 2-4 of the method (FIG. 1B) relate to aspects of the initial clinical characterization which are performed in a clinic to characterize particular physiological aspects of the specific patient prior to formal implementation of a therapeutic regimen. Sensory threshold (S-thresh) identification (Step 2) is determined by identifying when patient first senses that stimulus is being applied. This characterization may be done through psychophysical testing or simply just turning intensity (pulse width/amplitude) until the patient reports that it is being felt. Movement threshold (M-thresh) is identified (Step 3) as the intensity when the diaphragm movement is visualized or palpated. Functional threshold identification (Step 4) relates to identifying the stimulation intensity threshold (F-thresh) that elicits inspiration at a level that is sufficient to functionally ventilate the patient during sleep. These steps may all be considered aspects of the method, as provided by the invention, where patient-specific data are collected and then used as input that determines aspects of a therapeutic regimen that are related both to the ramp up profile of stimulation and the stead state level of stimulation.

Steps 5-7 of the method (FIG. 1B) relate to a sequence of events that follow after the patient turns on the therapeutic device prior to going to sleep until a time when sleep actually begins. As such, these various steps relate to aspects of an initial phase of stimulating the diaphragm in a therapeutic regimen. Step 5 refers to the initiation of events that occur immediately after a decision to go to sleep has been made, or as a healthcare provider observes that patient is preparing to go to sleep, or sleep is inevitable, whether intentionally or not. In Step 6, the stimulus intensity is cyclically ramped up over the duration of a predetermined amount of time to accommodate the sensory perception up to a threshold (determined in Step 2) that is likely to prevent the onset of sleep. The sleep onset time may be predetermined from polysomnographic (PSG) studies or set by the patient upon initiation (i.e. an adjustable sleep time). Alternatively, sleep may be detected through a sleep-detection algorithm with the cycle time completing with detection of sleep. Still further, sleep onset may be noted by observation of an attending health care professional.

Steps 8-11 (FIG. 1B) of the method relate to steps that occur after sleep has begun. Once sleep is achieved a sequence of events (Step 8) is initiated such that the patient synchronizes his or her natural breathing to the rate being paced by the electronic signal generator. The stimulus intensity is cyclically ramped up from the sensory threshold to the movement threshold (Step 9). This signal ramping allows the patient's innate breathing to synchronize with the stimulated breathing, as such, synchronization is an aspect of the method performed by the patient. Synchronization occurs naturally and has been consistently observed to occur in patients with ALS who exhibit volitional breathing who have been implanted with a DPS. The time of synchronization can be predicted or estimated from studies that monitor the diaphragm EMG and determine when innate activity is consistently synchronized with DPS. Alternatively, the stimulation can be presented following the detection of innate breathing activity. Step 10 refers to a decision point which requires an affirmative response before moving on to Step 11. In the absence of synchronization, Step 9 continues.

Step 11 (FIG. 1B) relates to activity that occurs after synchronization has been achieved, when the stimulus intensity can be ramped up to a functional level to ventilate the patient. Alternatively, if the diaphragm EMG is detected for synchronization, the absence of activity can cause the stimulus intensity to elicit a functional contraction. Absence of activity can be predetermined as a time equivalent to the definition of an apneic event (i.e. 10 seconds) or a time based on the periodicity of prior breathing.

As described above, parameters that are individually adapted to the patient during an early phase of the method 202 (FIG. 1A) generally allow a comfortable merging of electrically-paced breathing into a natural course of sleep onset and continuing through the sleep cycle of a patient who is not on full time pacing. One feature of the method that allows this comfortable merger is the delay in onset of the pacing until an appropriate time after the patient has begun to sleep. Thus, in some embodiments of the method, the stimulation protocol includes an onset delay period before the onset of stimulation (e.g., approximately 5 minutes, 10 minutes, 20 minutes, 30 minutes, etc.).

Another feature of the method that supports merging of the patient's normal breathing with paced breathing during sleep includes ramping of stimulation of the patient's diaphragm to support breathing, as it occurs at various phases of the method. The role of ramping is at least two-fold. In one aspect, ramping serves the purpose of not interrupting or disturbing the onset of sleep. In another aspect, stimulation level ramping serves to allow a synchronization of the patient's own breathing rate to the rate being driven by pacing stimulation. Ramping the electrical stimulation of the diaphragm may occur in various forms, such as increasing pulse duration and then increasing pulse amplitude, increasing pulse amplitude and then increasing pulse duration, or increasing pulse amplitude and pulse duration in an interleaved manner. With regard to the general form of the ramping, ramping may occur with a linear envelope, with an exponential envelope, or with an envelope of an arbitrary or irregular shape.

Figure 2A:
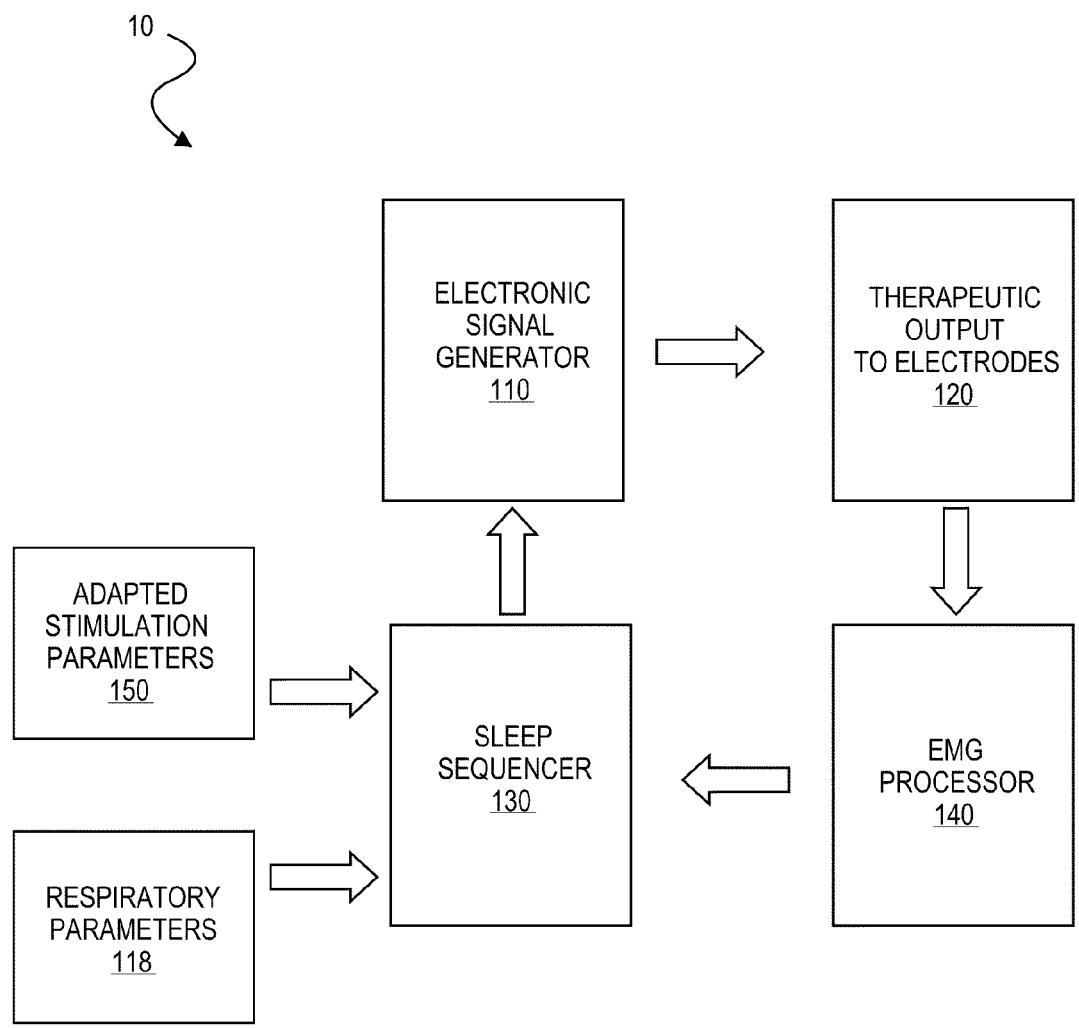
FIG. 2A provides a simplified block diagram of a system for implementing the method.

Embodiments of the method for improving sleep disordered breathing may be implemented by a system 10 which will be described first in general terms, as shown in FIG. 2A, and then depicted (FIG. 2B) and described in more detail below. Embodiments of the system 10 typically include various primary subsystems. One subsystem is represented by an apparatus or assembly of components that act as an electronic signal stimulator or diaphragm pacing system (DPS) 110 (including components surrounded by a dotted line) that provides electrode-delivered stimulation to the diaphragm of a patient to regulate the patient's breathing. An example or typical embodiment of apparatus 110 is provided by the NeuRx DPS™ System (Synapse Biomedical, Inc. of Oberlin, Ohio), which includes electrodes to deliver the stimulation to the target, a stimulation device to generate charge balanced waveforms, a microprocessor to format and coordinate stimulus delivery, and various peripheral components that embody the device. The output 120 of the electric signal generator 110 is directed to electrodes implanted in the diaphragm of the patient, which control the breathing rate.

A sleep sequencer processor 130 represents another subsystem, which may be a separate device or a component incorporated into the main apparatus of the DPS System that includes the electronic signal generator, provides the appropriate cyclic timing to ramp between the thresholds identified in the method as shown in FIG. 1B. The sleep sequencer 130 may use observation- or experience-based settings or a user adjustable input to determine the timing of the onset of sleep. Sequencing from the sensory threshold to the movement threshold may be accomplished by providing the appropriate cyclic timing to ramp stimulation based on a experience-based setting, or it may use the detection of electromyographic diaphragm activity in the contralateral diaphragm upon delivery of stimulation and an absence of electromyographic activity without stimulation to sense if the innate breathing has synchronized with the stimulation. Finally, the sleep sequencer may ramp stimulation up to the functional threshold to elicit functional contractions to ventilate the patient. The functional contraction may be set to the same stimulation level as the movement threshold. Alternatively, once the sensory threshold is achieved, the sleep sequencer may be set to deliver functional stimulation in the absence of electromyographic activity when inspiration should be occurring, i.e. during a central apneic event.

Representing still another component subsystem, the system may also include electromyographic activity sensing component 140 which receives diaphragm EMG activity data from the electrodes implanted in the patient diaphragm. This electromyographic activity may be processed and displayed for manual use in manual operation of the system in a monitored clinical setting or EMG data may be fed into the DPS System or sleep sequencer to automate the apparatus. In a monitored clinical setting the absence of diaphragm activity, when inspiration should be occurring (e.g. within 10 second of the last recorded activity), could be used as a diagnostic tool and be coupled with the further intervention of application of the diaphragm stimulation.

Features of the system described above in general terms will now be described in greater detail with reference to FIG. 2B, and in a manner that tracks the flow of electrical signals. In one embodiment, the electrical signal generator 110 shown may be configured to generate pulses and/or signals that may take the form of sinusoidal, stepped, trapezoidal waveforms or other relatively continuous signals. The electric signal generator 110 may include one or more channels that can independently control the amplitude, frequency, timing and pulse width of the corresponding electrodes connected thereto. In one embodiment, the electrical signal generator 110 can be an external signal generator that is electrically connected to or in electrical communication with the electrodes. Example of a suitable electrical signal generator include a NeuRx RA/4 stimulator of the NeuRx DPS™ System (Synapse Biomedical, Inc. of Oberlin, Ohio), which are four-channel devices with independent parameter programmability, that can, accordingly independently control up to four electrodes. In an alternative embodiment, the electrical signal generator 110 can be an implantable signal generator. One suitable example of a fully implanted signal generator is the "Precision" electrical signal generator available from Boston Scientific/Advanced Bionics. One example of a partially implanted radio-frequency signal generator system is the "XTREL" system available from Medtronic, Inc.

Figure 2B:
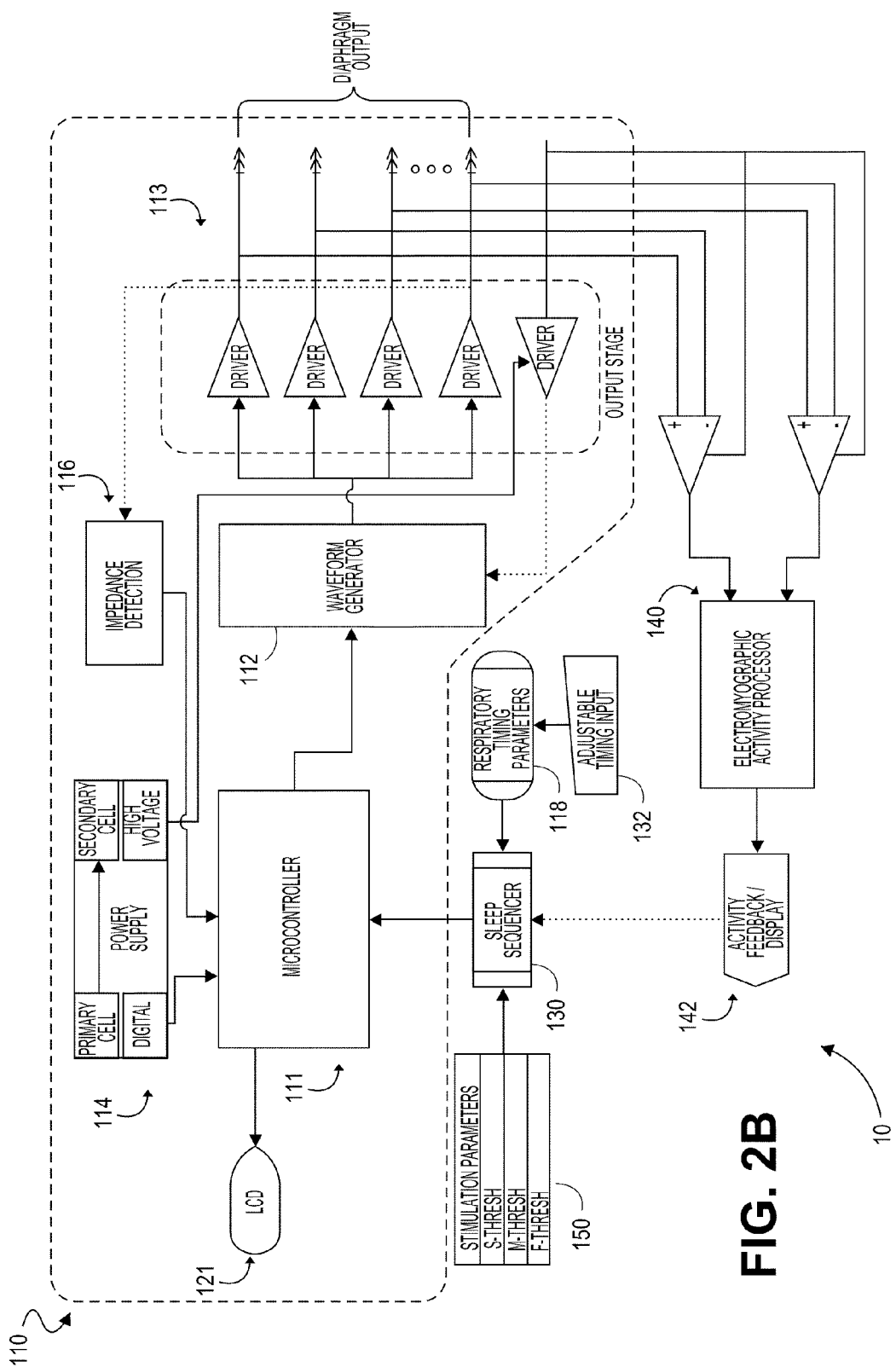
FIG. 2B provides an overview and further detail of a system for implementing the method.

The electrical signal generator 110 depicted in FIGS. 2A and 2B is comprised of several blocks to produce a coordinated stimulus output. The core of the electrical signal generator 110 is a supervisory microcontroller 111 that coordinates parameter and sensed inputs, display, and stimulus/trigger outputs. The stimulus and timing parameters are stored in non-volatile memory and are programmed specifically for the respiratory support needs and desired electrode features for the particular patient. A waveform generator 112 assembles the control signals from the microcontroller in the necessary waveform patterns to be conveyed through the output stage signal drivers 113. The microcontroller 111 receives power from a power supply 114. It receives input of sensing information 115, impedance detection 116, timing parameters 118 and stimulation parameters 150 and EMG data 142, all by way of a sleep sequencer 130. The microcontroller 111 provides output to a trigger output 119 and an LCD 121, in addition to the waveform generator 112. The output stage comprising drivers 113 also provide output to the impedance detector 116. The drivers 113 provide output in the form of stimulation of the electrodes 120.

With further reference and in greater detail regarding the sleep sequencer 130, electromyographic signals from electrodes 120 implanted in the diaphragm are collected and conveyed to an electromyographic processor 140. The processor 140, in turn, can both display resulting EMG data (available for clinical review by a health care professional) and transmit data to a sleep sequencer 130. The sleep sequencer 130 has already received stimulation parameter values input 150 that were collected during an early aspect of the method, when parameter adaptation studies were run on the patient (Steps 2, 3, and 4 of FIG. 1B). The sleep sequencer further receives input 188 regarding respiratory timing parameters, which may include a manually adjustable timing input 132. The sleep sequencer thus integrates information regarding the parameter adaptations, stimulus level ramping, respiratory timing, and EMG feedback from the diaphragm while it is being paced by the electrical signal generator assembly. (It may be appreciated that these feedback data do not include EMG data from the diaphragm that are associated with independent breathing effort.) Further, it can be appreciated that input regarding the stimulation parameters 150 and the respiratory timing parameters 118 can be adjusted or revised during the therapeutic regime, based on changes in the status of the patient and observation These data are integrated by the sleep sequence 130 and conveyed to the microcontroller 111.

In some embodiments, the output of drivers 113 is a capacitively-coupled current-regulated biphasic waveform. With each stimulus output, the circuit impedance is detected and fed back to the microcontroller to display electrode circuit integrity. The microcontroller may be driven to send the control signals to the waveform generator from an external sensed source (either a digital level or analog signal, such as diaphragm EMG) or from internal timing that is based on the stored timing parameters. The microcontroller may also be programmed to send out an analog or digital trigger signal to an external device based on a programmed sequence or event.

In one example, the electrical signal generator can supply the implantable electrodes with an electrical signal that serves as electrical stimulation to the respiratory system of the patient. For example, the electrical signal can be a capacitively-coupled, charge balanced, biphasic, constant current waveform with adjustable parameters as shown below in Table 1. It will be appreciated that the electrical signal can take the form of other waveforms for electrical stimulation such as monophasic or rectangular biphasic.

TABLE 1

| Parameter | Range |
| --- | --- |
| Stimulation Interleave Rate | 1-100 |
| Trigger Delay (from inspiration) | 1.0-4.0 s |
| Stimulation Time | 0.8-1.5 s |
| Output Pulse Period | 20-250 ms |
| Pulse Width Modulation Count | 0-10 |
| Cathodic Current Amplitude | 5-25 mA |
| Cathodic Current Pulse Width | 20-200 µs |
| Voltage | 0-65 V |
| Pulse Frequency | 10-20 Hz |

Although the stimulatory signal can be delivered to a variety of locations in the body of a patient to stimulate the respiratory system, in one example, the electrical stimulatory can be delivered to the diaphragm of the patient, through the electrodes, continuously or periodically, as the patient is falling off to sleep and during sleep. For example, the electrical stimulation can be delivered to the diaphragm of the patient at specified intervals, for a certain period of time per interval. In typical embodiments of the method, the stimulation is delivered constantly, albeit at rates and intensity that vary between the initial phase of sleep and the stable portion of sleep.

The external electrical stimulator makes use of one or more intramuscular electrodes that are suitable for implanting into muscle tissue. In some embodiments, the intramuscular electrode can serve as a cathode. In some embodiments, the electrode is particularly adapted for temporary implantation. Examples of appropriate electrodes and their features are described in detail in U.S. patent application Ser. No. 11/716,459 of Ignagni, entitled "Ventilatory Assist System and Methods to Improve Respiratory Function", as filed on Mar. 9, 2007 (now U.S. Pat. No. 7,962,215), which is incorporated herein in its entirety by this reference.

The inventive system and method have been developed and tested on patients under appropriate protocols and safety guidelines. FIGS. 3-5 provide examples of the human subject data that have been collected. Exemplary electromyographic recordings are shown in FIGS. 3A and 3B that were obtained from an ALS patient that had been implanted with pacing electrodes 18 months prior to the time these recordings were made. The two sets of traces show the electromyographic recording from right and left hemi-diaphragms. (There is a difference between the right and the left traces that is a result of differences in placement; that difference does not distract from the significance of the data as they relate to reflecting EMG activity.) In FIG. 3A a depressed, low level, electromyographic recording is shown during a period of normal awake breathing. In FIG. 3B a significant increase in the magnitude of the electromyographic recording is shown during a period of maximally volitional breathing. This demonstrates the ability of the system to detect electrode myographic activity and to differentiate the amount diaphragm movement based on magnitude of electromyographic recordings. An absence of activity or a minimal of activity may be used to as diagnostic criteria or feedback indicating an insufficient diaphragm contraction.

Figure 4A:
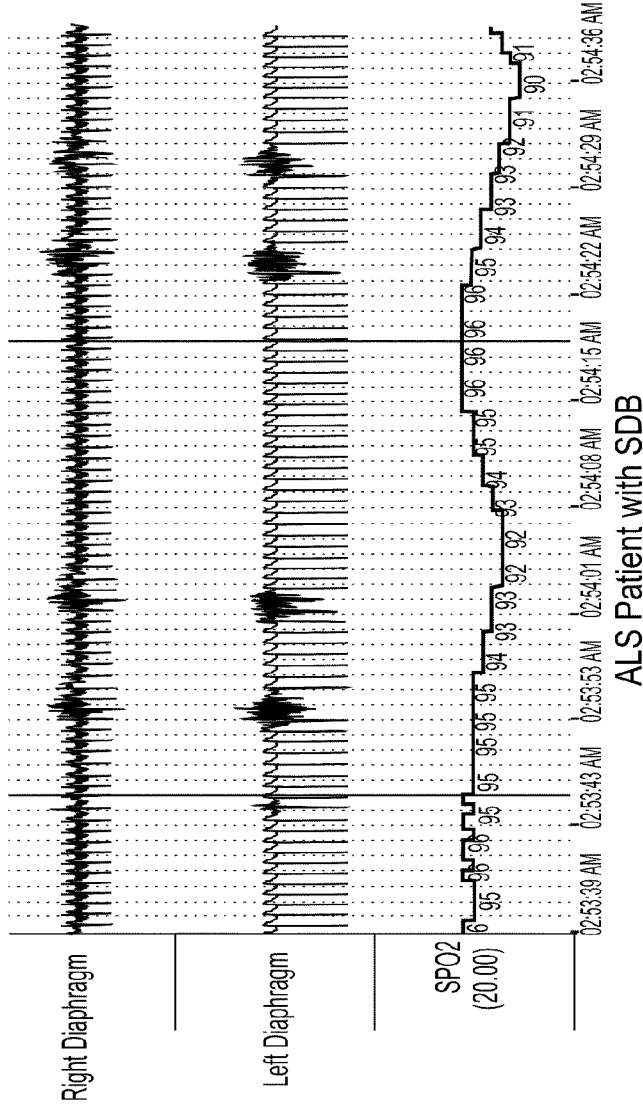
FIGS. 4A and 4B provide two EMG charts showing sleep breathing of an ALS patient with sleep disordered breathing.
Figure 4B:
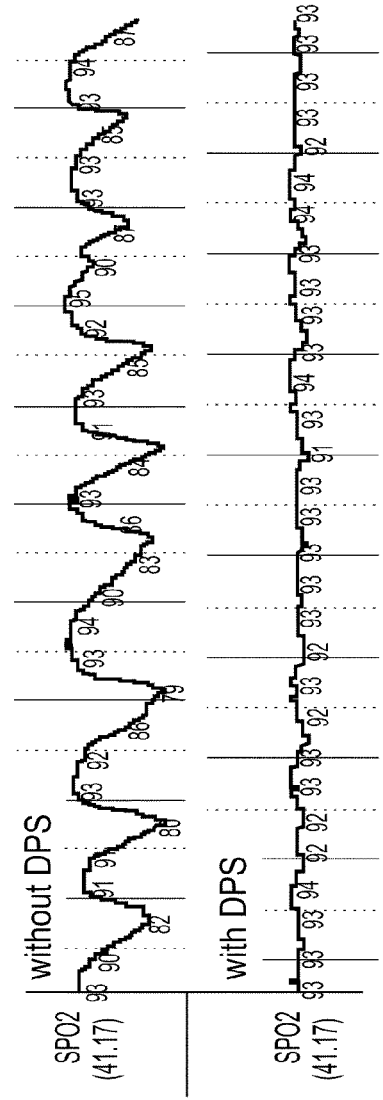

An exemplary episodic view of sleep disordered breathing in an ALS patient, exhibiting deficits in upper motor neuron function is shown in FIGS. 4A and 4B. The upper panel (FIG. 4A) shows a Cheyne-Stokes type breathing pattern with the right and left hemidiaphragms exhibiting apneic events followed by two quick bursts of diaphragm activity followed by another apneic event and two quick bursts of diaphragm activity. The bottom trace of the upper panel (FIG. 4A) shows the pulse oximetry ($SPO_2$) fluctuating, as expected, following the apneic events. The upper trace of the lower panel (FIG. 4B) shows the patient without the support of DPS demonstrating respiratory instability as evidenced by the ongoing oscillation of the pulse oximetry. The patient shows resolution of the respiratory instability with the addition of DPS, in the bottom trace.

An example of processing electromyographic activity of an ALS patient is shown in FIGS. 5A and 5B. In this case, the sampled electromyographic activity was processed by filtering to remove the undesired EKG signal, rectified, and then an average magnitude of the signal amplitude was calculated. Data were collected at two time points 11 weeks apart (FIG. 5A at the outset of the study, FIG. 5B after 11 weeks of therapy). In the example shown, the electromyographic activity is seen to increase over time with conditioning of the diaphragm in a patient experiencing respiratory insufficiency. These EMG data correlated well with fluoroscopy data showing diaphragm movement. Similarly the amplitude of the activity can be used to discriminate a functional contraction from a non-functional contraction.

In another example, a clinical study was run to evaluate the effect of diaphragm pacing treatment, in accordance with the inventive method, on patients with neuromuscular disease who had disordered sleep patterns and disordered breathing during sleep. The results of the study suggest that benefits may derive from the treatment; accordingly, some general observations and considerations will be described, and some relevant data will be provided below.

Patients that cannot readily tolerate non-invasive positive pressure ventilation (NIPPV) may be particularly benefited by the methods and systems described herein. Considerations that particularly recommend the use of this inventive therapeutic method for these patients are indications that NIPPV may actually accelerate the deconditioning of the diaphragm and the dependence of ALS patient on increasing amounts of NIPPV (Aboussouan, et al., "Effect of noninvasive positive pressure ventilation on survival in amyotrophic lateral sclerosis". Ann Intern Med 1997; 127: 450-453). The trade off between the benefit of immediate assistance in breathing against the acceleration the disease progression is, of course, very undesirable. Combining diaphragm pacing stimulation (DPS) therapy with NIPPV may slow or eliminate this nocturnal deconditioning of the diaphragm, and further slow the patient's progression toward complete dependence on NIPPV support. Before implementation of diaphragm pacing stimulation, particularly during sleep, various operational parameter settings for diaphragm pacing stimulation that provide a level of respiratory assistance without arousing the patient from sleep may be determined.

Embodiments of the DPS method, as provided herein, typically involve the implanting of a DPS device and an extended period of DPS therapy. The diaphragm pacing stimulation includes sufficient stimulation to initiate a breath and further stimulation sufficient to support a breath to completion. As described herein, the method may be adapted for the therapeutic application of improving the quality of sleep, and may be further adapted to the physiological and temperamental particulars of each patient (Steps 2-4 of FIG. 1). These adaptations for diaphragm pacing during sleep may include, for example, any one or more of a delay of stimulation onset to allow patient to fall asleep, a gradual ramping of diaphragm stimulation level over time after onset of stimulation, setting a steady state level of stimulation so as to minimize arousal from sleep, and the monitoring of diaphragm EMG during system use.

A programmable delay in the onset of stimulation, merely by way of example, may be set for an interim of 15 seconds to 30 seconds after initiation of sleep. A ramping period after initiation of electrode stimulation may be, merely by way of example, of about 30 minutes, wherein a minimal stimulation is provided at the outset, and a plateau level of stimulation is reached at 30 minutes, and such plateau level is continued through the sleep period. Further, a sleep-appropriate plateau level of respiration may be set that permits sleep without awakening, such level, as driven by diaphragm pacing may be set, merely by way of example, within a range of about 8 to 20 respirations per minute.

Additionally, the stimulus frequency may be set such that the delivered stimulation is at a level to produce fused contractions of the diaphragm muscle. The fusing of contractions in a diaphragm, which is composed primarily of slow twitch type JIB muscle fiber, will exhibit unfused contraction at a low frequency. A threshold level of stimulation is required to elicit a desirable and sustainable fused contraction. Accordingly, the frequency may be ramped up over the initiation period to produce a more forceful contraction while remaining below a level that would cause the patient to awake. Increases in delivered stimulus may be performed based on the charge (the product of pulse duration and amplitude) delivered on a pulse-by-pulse basis. By initiating each inspiration with a very gradual ramping, the stimulus may be delivered slowly, and then increased with a steeper ramp to create a greater inspiratory pressure and thus greater volume for each breath. Following a determination and setting of stimulation parameters that have been adapted or optimized for sleep, a therapeutic regimen of diaphragm stimulation may be implemented.

The implanted DPS electrodes may be used to record diaphragm EMG during the polysomnographic recording, or they may be used in a stand alone manner to determine the amount of diaphragm activation during a diagnostic sleep session. In either context, the EMG data may provide a physician with information that allows an evaluation of the disease state and the efficacy of the diaphragm pacing in improving sleep. In some embodiments of the method, the parameters that have been adapted to make the diaphragm pacing stimulation appropriate for sleep may be evaluated by a physician and revised in accordance with accumulated EMG data, or any other relevant clinical data. Following such revision of parameters adapted for stimulation of the diaphragm during sleep, a revised therapeutic regimen may be implemented.

It can be noted that although it may be technically feasible to include a feedback loop in the method, whereby patient initiated breathing effort during sleep would be incorporated into the control of breathing by DPS. In the view of the inventors, however, this approach appears disadvantageous for several reasons, including the complexity and likely temperamental or unstable nature of such a method that included such feedback, the associated burden of training physicians in the method, and the cost of the system. On the whole, inventors believe that a system that operates under the discretionary control of health professionals exercising clinical judgment with an open loop implementation (instead of the automatic control of a voluntary respiratory effort feedback loop) offers an approach that makes the method safe, robust, and effective. Accordingly, a feedback loop that incorporates patient-initiated breathing effort data as feedback into the system control is not included in the inventive method.

In the clinical study referred to above, twelve of the 16 ALS patients had bulbar symptoms, such symptoms being consistent with poor tolerance of noninvasive positive pressure ventilation therapy. At the time of implant of the DPS device, the patients had a median forced vital capacity (FVC) of 57% of the predicted value, and a median score of 26 on the ALS Functional Rating Scale-revised (ALSFRS-R). The study patients have a mean survival from diagnosis of 3.0±0.7 years. From reports in the literature (Louwerse, et al., "Amyotrophic lateral sclerosis: morality risk during the course of the disease and prognostic factors". Publications of the Universiteit van Amsterdam, Netherlands. 1997), the median survival time from diagnosis was 1.4 years (95% confidence interval, 1.3-1.6 years).

This clinical study also yielded observations that indicate that ALS patients may be more tolerant of DPS than NIPPV, and that they can make use of the DPS stimulation for extended periods to improve their breathing, which may improve the quality of their sleep. A few of patients in the pilot study voluntarily switched from BiPAP therapy to DPS because of their perception of greater ease in breathing. For example, some patients have fallen asleep while using the DPS system and reported that they then slept better than they had in some time.

Another measure of outcomes in ALS is provided by the revised Functional Rating Scale (ALSFRS-r). This is a disease-specific scale that measures global function as grouped around several elements such as limb function, bulbar function, and respiratory function. The slope of ALSFRS over time has a greater correlation with survival than does the slope of forced vital capacity. In a large retrospective clinical study the effects of Neurontin, it was found that three groups of patients could be classified by the rate of progression of their ALSFRS-r score. Slowly progressing patients (patients with a rate of decline less than −0.44 ALSFRS units per month) had median survival of more than 3 years, moderately progressing patients (patients with a rate of decline between −1.04 and −0.44) had a median survival of 2.3 years, and rapidly progressing patients (patients with a rate of decline greater than −1.04) had a median survival of 1.3 years. Performing a paired comparison of the rate of decline of patients in the DPS clinical study performed by the inventors yields an average survival improvement of 9 months (p=0.03).

As the diaphragm is the principal (or sole) respiratory muscle active during REM sleep, reduced or lost function of this muscle leads to sleep irregularities with fragmentation by multiple arousals and awakenings. Polysomnographic recordings of sleep with and without rhythmic diaphragm pacing stimulation demonstrate this effect. Overnight EMG recordings of the diaphragm with nocturnal pulse oximetry in ALS patients implanted with the NeuRx DPS™ System demonstrate that low levels of blood oxygen are associated with depressed diaphragm contraction.

It should also be understood that this therapeutic method may be applied in patients who are being treated more generally for ALS and hypoventilation, and with goals directed toward improving ventilation and the quality of life. Accordingly, for example, a primary efficacy endpoint of improvement in breathlessness may be measured using the Modified BORG Scale. This unidimensional, health related, quality of life instrument provides a recognized, reproducible measure of physical effort, and more specifically in this context, the intensity of the sensation of breathing effort or breathlessness. Measurements can be made, as the patient is able, without support (i.e., without NIPPV or DPS) and in combinations of support. These measurements can be recorded prior to implantation of the DPS electrodes for baseline data, and then at regular intervals following the initiation of DPS treatment. Other endpoints include the daily use of DPS and NIPPV, as patients will record categorized hours used of each therapy and the weekly preference for ventilation therapy on the log form. Finally, a measure of nocturnal hypoventilation can be performed at regular week intervals by recording the nighttime $SpO_2$ with a software-driven recording system such as Crystal PSG™ device. The nocturnal oxygen desaturation index (ODI) and the % of monitoring time spent in hypoxia (SpO2<90%) pre-implant and post-implant can be calculated. The ODI represents the number of times per hour of monitoring that the SpO2 desaturates by more than 4%. Measurements of breathlessness and ODI can be made under consistent conditions with respect to the patients' use of supplemental oxygen and will be made with and without DPS.

In addition to ALS patients, other types of patients could benefit from DPS supported breathing during sleep. Any patient, for example, with upper motor neuron dysfunction, even in conjunction with lower motor neuron dysfunction that results in temporary or permanent diaphragm paralysis is an appropriate candidate for DPS therapy. Periodic respiratory instability, as demonstrated in patients with central sleep apnea and congestive heart failure are prime candidates for DPS intervention. Other examples of diaphragm paralysis have been reported in patients with Charcot-Marie-Tooth disease, associated with diabetes mellitus, spinal cord injury, poliomyelitis, Guillain-Barre' syndrome, diabetes, diphtheric neuropathy, beriberi, alcoholic neuropathy, brachial plexus neuropathy, lead neuropathy, trauma, myotonic dystrophy, Duchenne's muscular dystrophy, paraneoplastic syndrome, and idiopathic conditions.

By way of further examples, post surgical patients that are at risk of mechanical ventilation in the intensive care unit (ICU) may benefit from monitoring and intervention. An example of an at-risk surgical population would include bariatric patients. These patients, because of their obesity are already prone to sleep dysfunction and often have difficulty with the recovery and regulation of $CO_2$ as a result of a laparoscopic surgical procedure for their obesity. An evaluation period according to Steps 2-4 of the method (FIG. 1) may appropriately be performed prior to surgery in order to obtain patient specific parameter values. A typical bariatric procedure involves work at or around the diaphragm, and thus could easily include placement of intramuscular electrodes in the diaphragm for subsequent monitoring of diaphragm EMG activity during recovery. If sporadic diaphragm contraction is observed by ICU staff, then rhythmic diaphragm contraction would be commenced to avoid apneas and potential intubation for the patient. Stimulation would then proceed throughout the night, until the patient awakens and diaphragm respiration can be supplemented with intercostal and accessory muscle respiration under volitional control centers of the patient.

Unless defined otherwise, all technical terms used herein have the same meanings as commonly understood by one of ordinary skill in the art to which this invention belongs. Specific methods, devices, and materials are described in this application, but any methods and materials similar or equivalent to those described herein can be used in the practice of the present invention. While embodiments of the inventive device and method have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, while some theoretical considerations have been advanced in furtherance of providing an understanding, for example, of ways that embodiments of the invention beneficially intervene in the physiology of muscles and neural pathways responsible for breathing, and the role of this physiology in sleep, the claims to the invention are not bound by such theory. Moreover, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

What is claimed is:

1. A method for adapting a breathing pattern of a patient with disordered breathing toward a more healthful state to improve sleep, the method comprising:
    implanting a neurostimulatory device in a diaphragm of the patient;
    stimulating the diaphragm with the neurostimulatory device to establish an automatic, reflexive, or synchronized breathing mechanism;
    evaluating the patient's diaphragm by electromyographic (EMG) methodology to determine an effectiveness of establishment of the automatic, reflexive, or synchronized breathing mechanism;
    evaluating the patient by polysomnographic (PSG) methodology to assess diminishment of sleep disordered breathing; and
    using one or more of the evaluation by EMG methodology and the evaluation by PSG methodology to adapt the breathing pattern of the patient by modulating the stimulation of the diaphragm.

2. The method of claim 1 further comprising determining onset of sleep.

3. The method of claim 2, wherein determining onset of sleep includes monitoring a level of one or more physiological parameters.

4. The method of claim 3 further comprising determining when the level of one or more physiological parameters falls below a threshold value.

5. The method of claim 4, wherein the one or more physiological parameters is selected from the group consisting of a diaphragm EMG, an EEG and body movement.

6. The method of claim 1 further comprising:
    determining a movement threshold intensity, wherein the movement threshold intensity is a stimulation intensity when diaphragm movement is visualized or palpated; and
    waiting for a predetermined sleep onset time before ramping the stimulation intensity up to a movement threshold intensity.

7. A method for adapting a breathing pattern of a patient with disordered breathing toward a more healthful state to improve sleep, the method comprising:
    implanting a neurostimulatory device in a diaphragm of the patient;
    stimulating the diaphragm with the neurostimulatory device to establish an automatic, reflexive, or synchronized breathing mechanism;
    evaluating the patient's diaphragm by electromyographic (EMG) methodology to determine an effectiveness of establishment of the automatic, reflexive, or synchronized breathing mechanism;
    using the evaluation by EMG methodology to adapt the breathing pattern of the patient by modulating the stimulation of the diaphragm;
    determining onset of sleep;
    determining a sensory threshold intensity, wherein the sensory threshold intensity is a stimulation intensity where the patient first senses that stimulation is being applied; and
    ramping the stimulation intensity up to the sensory threshold intensity before onset of sleep.

8. The method of claim 7 further comprising:
    determining a movement threshold intensity, wherein the movement threshold intensity is the stimulation intensity when diaphragm movement is visualized or palpated; and
    ramping the stimulation intensity up to the movement threshold intensity after onset of sleep.

9. The method of claim 8 further comprising synchronizing the patient's natural breathing rate with a rate being paced by an electronic signal generator.

10. The method of claim 9 further comprising:
    determining a function threshold intensity, wherein the functional threshold intensity is a stimulation intensity that elicits inspiration at a level that is sufficient to functionally ventilate the patient during sleep; and
    ramping the stimulation intensity up to the function threshold intensity after the patient's breathing rate is synchronized with the rate being paced by the electronic signal generator.

11. The method of claim 10 wherein ramping up stimulation intensity comprises increasing pulse duration.

12. The method of claim 10 wherein ramping up stimulation intensity comprises increasing pulse intensity.

13. The method of claim 10 wherein ramping up stimulation intensity comprises increasing pulse duration and pulse intensity.

14. The method of claim 10 further comprising detecting an apneic event, wherein the apneic event occurs when at least about 10 seconds has elapsed since the previous inspiration.

15. The method of claim 14 further comprising delivering stimulation at the functional threshold intensity upon the detection of the apneic event.

16. A method for adapting a breathing pattern of a patient with disordered breathing toward a more healthful state to improve sleep, the method comprising:
    implanting a neurostimulatory device in a diaphragm of the patient;

stimulating the diaphragm with the neurostimulatory device to establish an automatic, reflexive, or synchronized breathing mechanism;

evaluating the patient's diaphragm by electromyographic (EMG) methodology to determine an effectiveness of establishment of the automatic, reflexive, or synchronized breathing mechanism;

using the evaluation by EMG methodology to adapt the breathing pattern of the patient by modulating the stimulation of the diaphragm;

determining a movement threshold intensity, wherein the movement threshold intensity is a stimulation intensity when diaphragm movement is visualized or palpated; and waiting for a predetermined sleep onset time before ramping the stimulation intensity up to a movement threshold intensity, wherein the predetermined sleep onset time is selected from the group consisting of approximately 5 minutes, 10 minutes, 20 minutes and 30 minutes.

17. A method for adapting a breathing pattern of a patient with disordered breathing toward a more healthful state to improve sleep, the method comprising:

initiating a sleep onset process prior to onset of sleep, wherein the sleep onset process comprises ramping a stimulation to a first level that does not exceed a level at which sleep is interrupted;

determining onset of sleep;

stimulating a diaphragm of the patient in a therapeutic regime after onset of sleep by gradually ramping the stimulation over time to reach a steady state level of stimulation to establish an automatic, reflexive, or synchronized breathing mechanism;

evaluating the patient's diaphragm by electromyographic (EMG) methodology to determine an effectiveness of establishment of the automatic, reflexive, or synchronized breathing mechanism; and using the evaluation by EMG methodology to adapt the breathing pattern of the patient by modulating the stimulation of the diaphragm.

18. A method for adapting a breathing pattern of a patient with disordered breathing toward a more healthful state to improve sleep, the method comprising:

initiating a sleep onset process prior to onset of sleep, wherein the sleep onset process comprises ramping a diaphragm stimulation to a first level that does not exceed a level at which sleep is interrupted;

determining onset of sleep; and stimulating a diaphragm of the patient in a therapeutic regime after onset of sleep by gradually ramping the stimulation over time to reach a steady state level of stimulation.

* * * * *